United States Patent [19]

Harnisch

[11] 3,985,763
[45] Oct. 12, 1976

[54] OXAZOLYL-ACETIC ACID DERIVATIVES AND OXAZOLYL-COUMARINES

[75] Inventor: Horst Harnisch, Leverkusen, Germany

[73] Assignee: Bayer Aktiengesellschaft, Leverkusen, Germany

[22] Filed: June 12, 1973

[21] Appl. No.: 369,124

Related U.S. Application Data

[63] Continuation of Ser. No. 154,652, June 18, 1971, abandoned.

[30] Foreign Application Priority Data

June 20, 1970  Germany............................ 2030507
Nov. 30, 1970  Germany............................ 2058877

[52] U.S. Cl. ..................... 260/307 D; 260/293.55; 260/293.58; 260/295 K; 260/295 F; 260/296 B; 260/307 F; 8/1 D; 260/243 B; 260/247.1 E; 260/247.2 A; 260/247.2 R; 260/250 G; 260/250 AC; 260/251 A; 260/256.4 F; 260/256.4 Q; 260/268 BC; 260/287 CF; 260/288 R

[51] Int. Cl.[2]........................................ C07D 413/04
[58] Field of Search.... 260/307 D, 293.55, 247.1 E, 260/247.2 A, 247.5 EP, 307 F, 247.2 R

[56] References Cited
UNITED STATES PATENTS

| 2,194,423 | 3/1940 | Friese | 260/267 |
|---|---|---|---|
| 2,990,405 | 6/1961 | Pepper et al. | 260/267 |
| 3,521,187 | 7/1970 | Snavely et al. | 260/307 D |

OTHER PUBLICATIONS
Color Index, 2nd Edition, 1956, vol. 2, p. 2901.
Color Index, 3rd Edition, vol. 4, pp. 4456–4457.
Lubs, The Chemistry of Synthetic Dyes and Pigments, 1955, pp. 242–245.

*Primary Examiner*—Nicholas S. Rizzo
*Assistant Examiner*—Mary C. Vaughn
*Attorney, Agent, or Firm*—Plumley and Tyner

[57] ABSTRACT

Oxazolyl-acetic acid derivatives of the formula

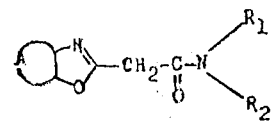

wherein
A represents the remaining members of an aromatic radical, and
$R_1$ and $R_2$ denote hydrogen, carbon-hydrogen radicals or together with the nitrogen atom form a heterocyclic ring, as well as their preparation and moreover oxazolyl-coumarines of the formula

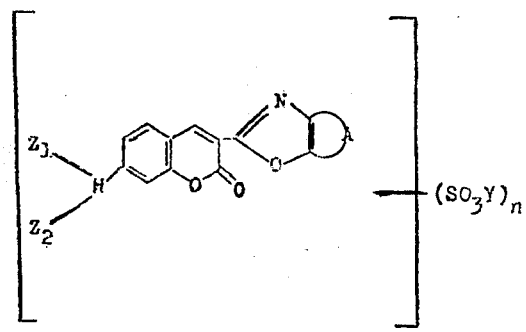

in which
A, $Z_1$ and $Z_2$ have the same meaning as above,
Y represents hydrogen or a cation,
$n$ represents a number 0, 1 or 2, and
the coumarine ring system can carry further substituents, with the proviso that in the case where $n$ denotes the number 0 and A represents an alkyl-substituted benzene radical, this alkyl substituent either possesses at least 2 C atoms or represents a methyl radical, as well as their preparation and their use as dyestuffs.

13 Claims, No Drawings

OXAZOLYL-ACETIC ACID DERIVATIVES AND OXAZOLYL-COUMARINES

This is a continuation of application Ser. No. 154,652 filed June 18, 1971, now abandoned.

The subject of the present invention are oxazolylacetic acid derivatives of the general formula

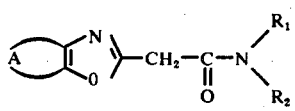

wherein

A represents the remaining members of an aromatic radical, and $R_1$ and $R_2$ independently of one another denote hydrogen, alkyl, cycloalkyl, aralkyl or aryl radicals, or together with the nitrogen atom, and optionally with the inclusion of further hetero-atoms as ring members, form a heterocyclic ring, and processes for their manufacture.

Possible aromatic radicals of which the residual members are designated A, are both radicals of monocyclic ring systems and radicals of condensed ring systems, which can be built up of aromatic-carbocyclic and/or aromatic-heterocyclic rings in any desired fusion arrangement, and which can optionally also contain condensed-on, partly saturated, rings. Five-membered and six-membered rings are preferred.

As examples of such aromatic radicals there may for example be mentioned: the radicals of benzene, naphthalene, tetralin, indane, anthracene, phenanthrene, acenaphthene, pyridine, quinoline, pyrimidine, quinoxaline, indazole and dibenzofurane, and amongst these the benzene radical and the naphthalene radical are to be regarded as particularly suitable.

These aromatic radicals can also possess substituents, such as alkyl, cycloalkyl, aralkyl, aryl, halogen, alkoxy, aryloxy, alkylcarbonylamino, arylcarbonylamino, alkylsulphonylamino, arylsulphonylamino, alkylsulphonyl, aralkylsulphonyl and arylsulphonyl radicals, and sulphamoyl and carbamoyl radicals which are preferably substituted by alkyl groups.

Phenyl and naphthyl radicals are preferentially to be understood by the abovementioned aryl radicals.

Suitable alkoxy radicals are above all those with 1 – 5 C atoms.

Possible alkyl radicals are especially those with 1 – 5 C atoms, which can possess further substituents, such as halogen, hydroxyl and alkoxy. Suitable alkyl radicals are, for example, methyl, ethyl, chlorethyl, bromethyl, hydroxyethyl, n-propyl, i-propyl and n-, i- and t.-butyl.

Suitable aralkyl radicals are especially the benzyl radical and the phenylethyl radical.

A suitable cycloalkyl radical is, for example, the cyclohexyl radical.

Possible alkyl radicals $R_1$ and $R_2$ are especially saturated and unsaturated alkyl radicals with 1 – 12 C atoms, which can be substituted by, for example, halogen, hydroxyl, $C_1$–$C_4$-alkoxy or $C_2$–$C_8$-dialkylamino groups, as well as by heterocyclic radicals, such as pyridyl, thienyl, furyl, tetrahydrofuryl, indolinyl, imidazolyl, 1,2,3-triazolyl, 1,2,5-triazolyl, 1,2,4-triazolyl, pyrrolidyl, piperazyl or morpholinyl radicals.

Heterocyclic rings which are formed by $R_1$ and $R_2$ via the nitrogen atom, optionally with the inclusion of further hetero-atoms as ring members, are preferably non-aromatic 5-membered to 7-membered N-heterocyclic structures, such as, for example, pyrrolidine, piperidine, azepine, pyrazoline, piperazine, morpholine, thiomorpholine-S-dioxide and indoline.

Suitable aryl radicals $R_1$ and $R_2$ are especially phenyl and naphthyl radicals, which can be substituted by halogen, such as chlorine and bromine, hydroxyl, $C_1$- to $C_4$-alkyl and $C_1$- to $C_4$-alkoxy.

The benzyl radical and the phenylethyl radical are above all to be understood by the aralkyl radicals $R_1$ and $R_2$.

Suitable cycloalkyl radicals $R_1$ and $R_2$ are cyclohexyl radicals optionally substituted by methyl radicals.

The new oxazole compounds of the formula I are obtained, according to the invention, if o-aminohydroxy compounds of the formula

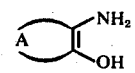

in which

A has the abovementioned meaning, are reacted with cyanoacetic acid amides of the formula

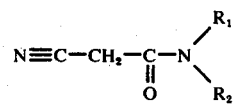

in which $R_1$ and $R_2$ have the abovementioned meaning, at elevated temperatures, optionally in an inert solvent and/or in an inert gas atmosphere.

It must be described as distinctly surprising that the reaction of II with III takes such a course, since it is known that the nearest comparable o-phenylenediamines react with cyanoacetamide, under comparable reaction conditions, in exactly the converse way, namely selectively with the carbonamide group to form the corresponding benzimidazole-acetonitriles (J. Am. Chem. Soc. 65, 1072 (1943)).

Additionally, the course of the reaction was not foreseeable since it is also known that nitrile compounds usually react relatively sluggishly with o-aminophenols in the absence of strong acids (J. Org. Chem. 9, 31 (1944)) and can, on the other hand, be reacted smoothly with carbonamides to give the corresponding benzoxazoles (compare, for example: J. Am. Chem. Soc. 17, 319 (1895); LIEBIGS Ann. 419, 74; Chem. Ber. 55, 1080 (1922)).

In carrying out the process according to the invention an appropriate procedure to follow is to react approximately equimolar amounts of the reactants II and III, in bulk or in a high-boiling organic solvent which is inert under the reaction conditions, at temperatures of 140° – 210° C, preferably 160° – 180° C, in a nitrogen atmosphere, until the evolution of $NH_3$ has ended (2 – 24 hours). An excess of one of the reactants in general has no influence on the desired course of the reaction.

Suitable o-aminohydroxy compounds of the formula II are, for example: 1-amino-2-hydroxybenzene, 1-amino-2-hydroxy-4-methylbenzene, 1-amino-2- hydroxy-5-methylbenzene, 1-amino-2-hydroxy-3,5-dimethylbenzene, 1-amino-2-hydroxy-4,5-dimethylbenzene, 1-amino-2-hydroxy-5-tertiary-butylbenzene, 1-amino-2-hydroxy-5-(1',1',3',3'-tetramethyl-butyl)-benzene, 1-amino-2-hydroxy-5-(β-methoxycarbonylethyl)-benzene, 1-amino-2-hydroxy-5-cyclohexylbenzene, 1-amino-2-hydroxy-5-chlorobenzene, 1-amino-2-hydroxy-5-fluorobenzene, 1-amino-2-hydroxy-benzene-5-carboxylic acid diethylamide, 1-amino-2-hydroxy-benzene-5-carboxylic acid morpholide, 1-amino-2-hydroxy-5-benzylbenzene, 1-amino-2-hydroxy-5-(phenylisopropyl)-benzene, 1-amino-2-hydroxy-5-phenylbenzene, 1-amino-2-hydroxy-5-methylsulphonylbenzene, 1-amino-2-hydroxy-5-ethylsulphonylbenzene, 1-amino-2-hydroxy-5-benzylsulphonylbenzene, 1-amino-2-hydroxy-5-phenylsulphonylbenzene, 1-amino-2-hydroxy-5-dimethylaminosulphonyl-benzene, 1-amino-2-hydroxy-5-diethylaminosulphonyl-benzene, 1-amino-2-hydroxy-5-[di-(n-butylamino)-sulphonyl]-benzene, 1-amino-2-hydroxy-5-(piperidyl-N-sulphonyl)-benzene, 1-amino-2-hydroxy-5-methoxy-benzene, 1-amino-2-hydroxy-5-phenoxy-benzene, 1-amino-2-hydroxynaphthalene, 1-amino-2-hydroxy-anthracene, 5-amino-6-hydroxyindane, 4-amino-5-hydroxy-acenaphthene, 3-amino-4-hydroxypyridine, 3-amino-4-hydroxy-quinoline, 7-amino-8-hydroxyquinoline, 3-amino-2-hydroxy-quinoxaline, 5-amino-1,3-dimethylbarbituric acid and 1-amino-2-hydroxy-dibenzofurane (obtainable by coupling diazotised sulphanilic acid with 2-hydroxy-dibenzofurane and subsequently reductively splitting the resulting azo dyestuff with sodium hydrosulphite in hot aqueous solution).

Suitable cyanoacetic acid derviatives of the formula II are, for example: cyanoacetamide, cyanoacetic acid methylamide, cyanoacetic acid ethylamide, cyanoacetic acid n-propylamide, cyanoacetic acid n-butylamide, cyanoacetic acid isobutylamide, cyanoacetic acid n-dodecylamide, cyanoacetic acid n-octadecylamide, cyanoacetic acid oleylamide, cyanoacetic acid 3-methoxy-n-propylamide, cyanoacetic acid 3-dimethylamino-n-propylamide, cyanoacetic acid 3-diethylamino-n-propylamide, cyanoacetic acid 2-hydroxyethylamide, cyanoacetic acid 3-chloro-n-propylamide, cyanoacetic acid 3-hydroxy-n-propylamide, cyanoacetic acid allylamide, cyanoacetic acid N-(2-aminoethyl)-ethanolamide, cyanoacetic acid N-methyl-N-(3-aminopropyl)-ethanolamide, cyanoacetic acid 3-n-butoxy-n-propylamide, cyanoacetic acid 3-N-morpholino-n-propylamide, cyanoacetic acid 2-(1',2',3'-triazolo)-ethylamide, cyanoacetic acid 2-(1',2',4'-triazolo)ethylamide, cyanoacetic acid 3-(1',2',5'-triazolo)-n-propylamide, cyanoacetic acid sulpholane-(3)-amide, cyanoacetic acid picolyl-(4)-amide, cyanoacetic acid furfurylamide, cyanoacetic acid tetrahydrofurfurylamide, cyanoacetic acid thenylamide, cyanoacetic acid cyclohexylamide, cyanoacetic acid isophorylamide, cyanoacetic acid benzylamide, cyanoacetic acid β-phenylethylamide, cyanoacetic acid dimethylamide, cyanoacetic acid diethylamide, cyanoacetic acid di-n-butylamide, cyanoacetic acid dibenzylamide, cyanoacetic acid N-methyl-ethanolamide, cyanoacetic acid diethanolamide, cyanoacetic acid dicyclohexylamide, cyanoacetic acid aziridide cyanoacetic acid pyrrolidide, cyanoacetic acid piperidide, cyanoacetic acid azepide, cyanoacetic acid N'-methylpiperazide, cyanoacetic acid N'-β-hydroxyethylpiperazide, cyanoacetic acid morpholide, cyanoacetic acid thiomorpholide-S-dioxide, N-cyanoacetyl-Δ²-pyrazoline, N-cyanoacetyl-2-methylindoline, cyanoacetic acid anilide, cyanoacetic acid p-toluidide, cyanoacetic acid p-chloranilide, cyanoacetic acid p-phenetidide, cyanoacetic acid 4'-chloro-p-phenoxy-anilide, cyanoacetic acid diphenylamide, cyanoacetic acid 1-naphthylamide, bis-cyanoacetic acid ethylenediamide, bis-cyanoacetic acid piperazide, bis-cyanoacetic acid 1,4-dicyclohexylamide, bis-cyanoacetic acid p-phenylenediamide and bis-cyanoacetic acid 4,4'-(diphenylmethane)-diamide.

The cyanoacetic acid amides of the formula III are in part known. These compounds are obtained by reaction of cyanoacetic acid methyl ester or ethyl ester with the appropriate amines of N-heterocyclics. In most cases it suffices to stir equimolar amounts of the components with one another, whereupon the particular amide compound forms in an exothermic reaction, and crystallises out. In the case of long-chain amines of the type of dodecylamine, oleylamine or octadecylamine, the reaction can be carried out by warming to 60° C for 1 hour. 3-Amino-sulpholane and piperazines were reacted at 80° – 100° C with cyanoacetic ester, and N-methylaniline, diphenylamine and 2-methylindoline were reacted at 180° C under nitrogen. Aromatic cyanoacetic acid amides such as cyanoacetanilide can be produced very smoothly (free of malonic acid diamides) from cyanoacetic acid and aromatic isocyanates in boiling anhydrous benzene or chlorobenzene, with $CO_2$ being split off. The cyanoacetamides of the formula II can advantageously also be reacted directly, without intermediate isolation, according to the invention, with the o-amino-hydroxy compounds of the formula II.

Suitable high-boiling, organic solvents for the reaction of II with III are: o-dichlorobenzene, s-trichlorobenzene, p-cymene, propylene glycol, diethylene glycol diethyl ether, glycol monomethyl ether-acetate, tetralin, decalin and diphenyldiphenyl ether mixtures.

One variant of the process for the manufacture of the new compounds of the formula I consists of reacting oxazolylacetamides of the formula

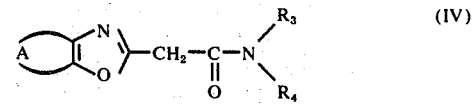

in which
A has the abovementioned meaning and
$R_3$ and $R_4$ represent hydrogen or the radical of an easily volatile hydrocarbon,
with amines of the formula

in which
$R_1$ and $R_2$ have the abovementioned meaning, which however differs from $R_3$ and $R_4$,
the group $-NR_3R_4$ being replaced by the group $-NR_1R_2$.

By the radical of an easily volatile hydrocarbon, an alkyl radical with 1 to 3 C atoms is especially to be understood.

As examples of the oxazolylacetamides of the formula IV which are suitable for the trans-amidisation, there may be mentioned: benzoxazole-(2)-acetamide, 5,6-dimethylbenzoxazole-(2)-acetic acid dimethylamide, 5-chlorobenzoxazole-(2)-acetic acid methylamide, 5-phenylsulphonyl-benzoxazole-(2)-acetic acid methylamide, 5-ethylsulphonyl-benzoxazole-(2)-diethylamide, 5-dimethylaminosulphonyl-benzoxazole-(2)-acetamide and naphtho-[1,2-d]-oxazole-(2)-acetic acid n-propylamide.

In practice, the trans-amidisation is for example carried out by heating one of the abovementioned compounds for several hours with the desired, preferably less volatile (boiling point >75° C) amine, to 130° – 180° C, optionally in one of the above-mentioned high-boiling, inert solvents or in an excess of the particular amine, and at the same time advantageously distilling off the easily volatile amine.

Amines suitable for trans-amidisation are, for example: n-butylamine, n-hexylamine, n-dodecylamine, N-morpholino-n-propylamine, 4-picolylamine, di-n-butylamine, benzylamine, β-phenylethylamine, cyclohexylamine, isophorylamine, piperidine, azepine, piperazine, N-methylpiperazine, morpholine, 2-methylindoline, tetrahydroquinoline, aniline, 3,4-dichloroaniline, N-methylaniline, diphenylamine, α-naphthylamine and dicyclohexylamine.

According to a further process, a special type of compounds is obtained, which, within the framework of the compounds of the formula I, have the general formula

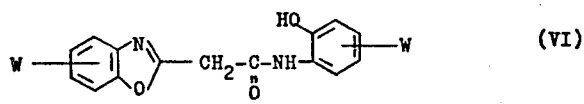

in which
W represents a subsitutent such as may be present on the abovementioned aromatic radicals A.

The process consists of reacting o-aminophenols of the formula

wherein
W has the abovementioned meaning, with a cyanoacetic ester of the formula

wherein
R denotes an alkyl radical with 1 – 4 C atoms or a benzyl radical,
optionally in an inert gas atmosphere and in a high-boiling, inert, organic solvent, at elevated temperatures, and in a molar ratio of 2 : 1, to give the compounds according to the invention of formula IV via the intermediate product

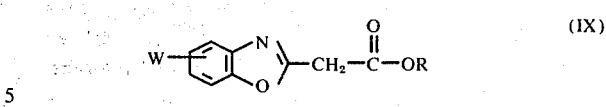

wherein
W and R have the abovementioned meaning.

In the case where W represents a 1st-order substituent, the molar ratio of the reactants has no influence on the course of the reaction, that is to say the desired product (VI) is always produced in a smooth reaction, without being able to isolate the intermediate product (IX).

An appropriate way of carrying out this process variant in practice is to heat the reactants VII and VIII to 140° – 180° C in a nitrogen atmosphere, and optionally in one of the above-mentioned high-boiling solvents, in the course of which evolution of $NH_3$ gas is first observed, and then to distil off the liberated alcohol via a column. In the case of o-aminophenols with 2nd-order substituents, the alcohol is only split off at 190° – 220° C.

This reaction course is also surprising, since, for the reasons explained above, it was not to be foreseen that the o-aminophenols VII would react, in a first stage, with the nitrile group of the cyanoacetic ester VIII, as is proved by the spontaneous evolution of $NH_3$ or — in the case of the o-aminophenols substituted by 2nd-order substituents — by the intermediate products IX which can be isolated.

The special compounds of the formula VI are also obtained by reacting benzoxazolylacetic acid esters of the formula IX with approximately the equimolar amount of an o-aminophenol of the formula VII, in a manner which is in itself known.

The new oxazole compounds of the formulae I or VI are colourless substances which — in most cases — melt without decomposition and dissolve easily in organic solvents. Because of their active methylene group, which is capable of coupling and of condensation, they are suitable for use as intermediate products for the manufacture of azo dyestuffs and methine dyestuffs as well as of optical brighteners. The new oxazole compounds of the formula I are of particular value as simply accessible and outstandingly suitable intermediate products for the manufacture of oxazolyl-coumarine compounds, which are, in turn, valuable fluorescent dyestuffs.

A further subject of the present invention are oxazolyl-coumarines of the general formula

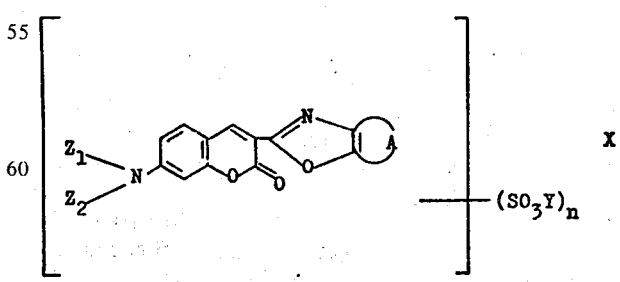

in which
A represents the remaining members of an aromatic radical, $Z_1$ and $Z_2$ independently of one another denote hydrogen, alkyl, cycloalkyl or aralkyl, or together with the nitrogen atom, and optionally with the inclusion of further hetero-atoms as ring members, form a non-aromatic heterocyclic ring, Y represents hydrogen or a cation, $n$ represents a number 0, 1 or 2, and the coumarine ring system can carry further substituents, with the proviso that in the case where $n$ denotes the number O and A represents the remaining members of an alkyl-substituted benzene radical, this alkyl substituent either possesses at least 2 C atoms or represents a methyl radical, as well as processes for their manufacture, and their use as fluorescent dyestuffs.

Possible aromatic radicals of which the remaining members are designated A, are both radicals of monocyclic ring systems and radicals of condensed ring systems, which can be built up of aromatic-carbocyclic and/or aromatic-heterocyclic rings in an optional fusion arrangement and which optionally also contain condensed-on, partly saturated rings. Five-membered and six-membered rings are preferred.

As examples of such aromatic radials there may, for example, be mentioned: the radicals of benzene, naphthalene, tetralin, indane, anthracene, phenanthrene, acenaphthene, pyridine, quinoline, pyrimidine, quinoxaline, indazole and dibenzofurane, amongst which the benzene radical and the naphthalene radical are to be regarded as particularly suitable.

These aromatic radicals can also possess substituents, such as alkyl, cycloalkyl, aralkyl, aryl, halogen, alkoxy, aryloxy, alkylcarbonylamino, arylcarbonylamino, alkylsulphonylamino, arylsulphonylamino, alkylsulphonyl, aralkylsulphonyl or arylsulphonyl radicals, and sulphamoyl and carbamoyl radicals which are preferably substituted by alkyl groups, as well as sulphonic acid groups.

Naphthyl and phenyl radicals are preferably to be understood by the abovementioned aryl radicals.

Suitable alkoxy radicals are above all those with 1 - 5 C atoms.

Possible alkyl radicals are especially those with 1 - 5 C atoms, which can possess further substituents, such as halogen, hydroxyl and alkoxy. Suitable alkyl radicals are, for example, methyl, ethyl, chloroethyl, bromoethyl, hydroxyethyl, n-propyl, i-propyl and n-, i- and t.-butyl.

Suitable aralkyl radicals are especially the benzyl radical and the phenylethyl radical.

A suitable cycloalkyl radical is, for example, the cyclohexyl radical.

Possible alkyl radicals $Z_1$ and $Z_2$ are especially saturated and unsaturated alkyl radicals with 1 - 5 C atoms, which can, for example, be substituted by cycloalkyl, halogen, nitrile, hydroxyl, alkoxy, carboxylic acid ester, alkylcarbonyl or dialkylamino groups, as well as by heterocyclic radicals, such as pyridyl, thienyl, furyl, tetrahydrofuryl, indolinyl, imidazolyl, 1,2,3-triazolyl, 1,2,5-triazolyl, 1,2,4-triazolyl, pyrrolidyl, piperazyl and morpholinyl radicals.

Possible heterocyclic rings which are formed by $Z_1$ and $Z_2$ via the nitrogen atom, optionally with the inclusion of further hetero-atoms as ring members, are preferably nonaromatic 5-membered to 7-membered N-heterocyclic structures, such as, for example, pyrrolidine, piperidine, azepine, pyrazoline, piperazine, morpholine, thiomorpholine-S-dioxide and indoline.

The benzyl radical and the phenylethyl radical are above all to be understood by the aralkyl radicals $Z_1$ and $Z_2$.

Suitable cycloalkyl radicals $Z_1$ and $Z_2$ are cyclohexyl and cyclopentyl radicals which are optionally substituted by methyl radials.

Suitable cations Y are: sodium, potassium, lithium and ammonium ions, as well as cations of basic dyestuffs.

Within the framework of the compounds of the formula X, those which correspond to the formula

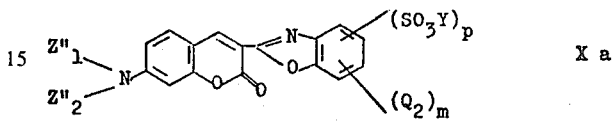   X a wherein $Q_2$ represents an unsubstituted $C_1-C_5$-alkyl radical, chlorine, $C_1-C_5$-alkoxy, cyclohexyl, phenyl, phenylalkyl, phenoxy, $C_1-C_5$-alkylcarbonylamino, phenylcarbonylamino, $C_1-C_5$-alkylsulphonylamino, phenylsulphonylamino, $C_1-C_5$-alkylsulphonyl, phenylsulphonyl, $-SO_2V_2$ or $-CONV_2$ radical, wherein V represents hydrogen or $C_1-C_2$-alkyl, $Z''_1$ and $Z''_2$ independently of one another denote hydrogen, an alkyl radical which is optionally substituted by chlorine, bromine, nitrile, hydroxyl or $C_1-C_4$ alkoxy, or the remaining members of a pyrrolidine, piperidine or morpholine radical, $p$ denotes 0 or 1 and $m$ denotes 0, 1 or 2, are particularly preferred.

The new coumarine compounds of the formula X can be manufactured according to various processes. One process is characterized in that o-hydroxyaldehydes or o-alkoxyaldehydes of the formula

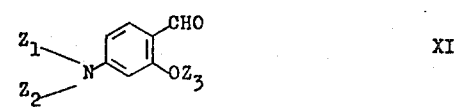   XI in which $Z_1$ and $Z_2$ have the abovementioned meaning, $Z_3$ represents hydrogen or an alkyl radical and the benzene ring can furthermore be substituted by a sulphonic acid group, and oxazolyl-2-acetic acid derivatives of the formula

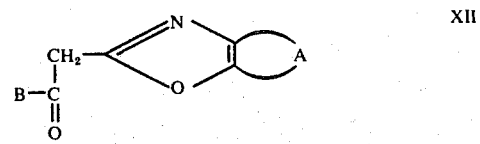   XII in which

A has the abovementioned meaning, with the proviso that in the case where A represents the remaining members of an alkyl-substituted benzene radical which is free of sulphonic acid groups, this alkyl substituent either possesses at least 2 C atoms or represents a methyl radical, and B represents an OH, alkoxy or aralkoxy group or the —NR$_1$R$_2$ group,
wherein
R$_1$ and R$_2$ independently of one another denote hydrogen, alkyl, cycloalkyl, aralkyl or aryl radicals or together with the nitrogen atoms and optionally with the inclusion of further hetero-atoms as ring members, form a heterocyclic ring,
are subjected to the aldol condensation, that cyclisation to give the coumarine is brought about, optionally after converting the o-alkoxy group into the hydroxyl group, and that this coumarine is thereafter sulphonated, if desired, in the case where starting materials free of sulphonic acid groups are used.

In general, the reactants XI and XII are employed in approximately equimolar amounts, but a slight excess of one of the compounds has no influence on the course of the reaction.

Possible aldehydes of the formula XI which are suitable for the reaction according to the invention are, for example: 4-dimethylaminosalicylaldehyde, 4-dimethylamino-5-methylsalicylaldehyde, 4-diethylamino-salicylaldehyde, 4β-cyanoethylmethylamino-salicylaldehyde, 4-hexahydrobenzyl-methylamino-2-methoxy-benzaldehyde, 4-β-cyanoethyl-methylamino-2-methoxybenzaldehyde, 4-phenyl-methylamino-2-methoxy-benzaldehyde, 4-di-(n-butyl)-amino-salicylaldehyde, 4-benzyl-methyl-aminosalicylaldehyde, 4-cyclohexylamino-salicylaldehyde, 4-(β-methoxyethyl)-methyl-amino-salicylaldehyde, 4-hydroxyethyl-ethyl-aminosalicylaldehyde, 4-n-propylamino-salicylaldehyde, 4-(β-chloroethyl)-methyl-amino-salicylaldehyde, 4-di-n-propyl-aminosalicylaldehyde, 4-(β-cyanoethyl)-amino-salicylaldehyde, 4-hydroxyethyl-methyl-amino-salicylaldehyde, 4-benzylaminosalicylaldehyde, 4-bromoethyl-amino-salicylaldehyde, 4-methoxyethyl-amino-salicylaldehyde, 4-(β-acetoxyethyl)-aminosalicylaldehyde, 4-(β-acetylethyl)-amino-salicylaldehyde, 4-N-pyrrolidyl-salicylaldehyde, 4-N-piperidyl-salicylaldehyde, 4-N-morpholinyl 4-acetamino-salicylaldehyde-anil and 4-(p-ethoxyphenyl)-methyl-amino-salicylaldehyde.

As suitable oxazolyl-2-acetic acid derivatives of the formula XII, there may for example be mentioned: benzoxazolyl-(2)-acetic acid ethyl ester, 5-methyl-benzoxazolyl-(2)-acetic acid methyl ester, 4,5-dimethyl-benzoxazolyl-(2)-acetic acid n-propyl ester, 5-chloro-benzoxazolyl-(2)-acetic acid ethyl ester, 5-bromobenzoxazolyl-(2)-acetic acid methoxyethyl ester, naphth[1,3-d]oxazolyl-(2)-acetic acid ethyl ester, naphth[2,3-d]oxazole-(2)-acetic acid methyl ester, 5-ethylsulphonylbenzoxazolyl-(2)-acetic acid ethyl ester, benzoxazolyl-(2)-acetamide, 5-methyl-benzoxazolyl-(2)-acetamide, 5-chlorobenzoxazolyl-(2)-acetamide, 5-ethylsulphonyl-benzoxazolyl-(2)-acetamide, 5-dimethylaminosulphonyl-benzoxazolyl-(2)-acetamide, 5-methyl-benzoxazolyl-(2)-acetic acid methylamide, 4,5-dimethylbenzoxazolyl-(2)-acetic acid methylamide, 5-cyclohexylbenzoxazolyl-(2)-acetic acid cyclohexylamide, 5-phenylbenzoxazolyl-(2)-acetic acid isophorylamide, naphth[1,2-d]oxazolyl-(2)-acetic acid methylamide, 5-methoxy-benzoxazolyl-(2)-acetic acid n-propylamide, 5-bromo-benzoxazolyl-(2)-acetic acid methylamide, 5-benzyl-benzoxazolyl-(2)-acetic acid methylamide, 5-(1',1',3',3'-tetramethyl-n-butyl)-benzoxazolyl-(2)-acetic acid anilide, 5-phenylsulphonyl-benzoxazolyl-(2)-acetic acid anilide, 5-benzylsulphonyl-benzoxazolyl-(2)-acetic acid methylamide, 5-diethylaminocarbonyl-benzoxazolyl-(2)-acetic acid n-butylamide, 5-methoxy-benzoxazolyl-(2)-acetic acid cyclohexylamide, 5-ethoxybenzoxazolyl-(2)-acetic acid anilide, 5-phenoxy-benzoxazolyl-(2)-acetic acid anilide, 5-acetylamino-benzoxazolyl-(2)-acetic acid 3'-methoxy-n-propylamide, 5-chloro-benzoxazolyl-(2)-acetic acid methylamide, benzoxazolyl-(2)-acetic acid n-propylamide, anthra[2,1-d]oxazole-(2)-acetic acid methylamide, phenanthreno[9,10-d]oxazole-(2)-acetic acid methylamide, acenaphth[5,4-d]oxazole-(8)-acetic acid methylamide, oxazolo[5,4-b]-pyridine-(2)-acetic acid anilide, oxazolo[4,5-g]quinoline-(2)-acetic acid methylamide, oxazolo[4,5-c]quinoline-(2)-acetic acid methylamide, oxazolo[5,4-d]-pyrimidine-(2)-acetic acid methylamide, oxazolo[4,5-d]pyridazine-(2)-acetic acid methylamide, oxazolo[4,5-b]quinoxaline-(2)-acetic acid methylamide, oxazolo[4,5-b]phenazine-(2)-acetic acid methylamide, 5-oxazolo[4,5-b]phenoxazine-(2)-acetic acid methylamide, oxazolo[4,5-a]dibenzofurane-(2)-acetic acid anilide, 5-methyl-benzoxazolyl(2)-acetic acid ethylamide, 5-methyl-benzoxazolyl-(2)-acetic acid n-propylamide, 5-methyl-benzoxazolyl-(2)-acetic acid 2'-hydroxyethylamide, 5-methyl-benzoxazolyl-(2)-acetic acid 3'-methoxy-n-propylamide, 5-methyl-benzoxazolyl-(2)-acetic acid 3'-dimethylamino-n-propylamide, 5-methyl-benzoxazolyl-(2)-acetic acid 3'-morpholino-n-propylamide, 5-methyl-benzoxazolyl-(2)-acetic acid 2'-bromoethylamide, 5-methyl-benzoxazolyl-(2)-acetic acid isobutylamide, 5-methyl-benzoxazolyl-(2)-acetic acid n-hexylamide, 5-methyl-benzoxazolyl-(2)-acetic acid benzylamide, 5-methyl-benzoxaxolyl-(2)-acetic acid 2'-phenylethylamide, 5-methyl-benzoxazolyl-(2)-acetic acid 4'-picolylamide, 5-methylbenzoxazolyl-(2)-acetic acid furylamide, 5-methyl-benzoxazolyl-(2)-acetic acid thenylamide, 5-methyl-benzoxazolyl-(2)-acetic acid tetrahydrofurfurylamide, 5-methyl-benzoxazolyl-(2)-acetic acid anilide, 5-methyl-benzoxazolyl-(2)-acetic acid 4'-toluidide, 5-methyl-benzoxazolyl-(2)-acetic acid 2'-hydroxy-5'-methylanilide, 5-chloro-benzoxazolyl-(2)-acetic acid 2'-hydroxy-5'-chloro-anilide, 5-tertiary butyl-benzoxazolyl-(2)-acetic acid 2'-hydroxy-5'-tertiary butyl-anilide, benzoxazolyl-(2)-acetic acid 2'-hydroxy-anilide, 5-methyl-benzoxazolyl-2)-acetic acid 4'-phenetidide, 5-methyl-benzoxazolyl-(2)-acetic acid 1'-naphthylamide, 5-methyl-benzoxazolyl-(2)-acetic acid dimethylamide, 5-methyl-benzoxazolyl-(2)-acetic acid diethylamide, 5-methyl-benzoxazolyl-(2)-acetic acid di-n-butylamide, 5-methyl-benzoxazolyl-(2)-acetic acid aziridide, 5-methyl-benzoxazolyl-(2)-acetic acid pyrrolidide, 5-methyl-benzoxazolyl-(2)-acetic acid piperidide. 5-methyl-benzoxazolyl-(2)-acetic acid azepide, 5-methyl-benzoxazolyl-(2)-acetic acid piperazide, 5-methyl-benzoxazolyl-(2)-acetic acid morpholide, 5-methyl-benzoxazolyl-(2)-acetic acid N-methylanilide, 5-methyl-benzoxazolyl-(2)-N'-methyl-N-piperazide and 5-methyl-benzoxazolyl-(2)-acetyl-2'-methyl-indoline.

The abovementioned oxazolylacetic acid derivatives are in part known. These compounds are obtained either according to processes which are in themselves known (compare, for example, Liebigs Ann. 537, 53 (1938); C.A. 67, 64 126m (1967); Chem. Ber. 100, 1661 (1967)) or — advantageously — according to the above-mentioned process of the invention, by condensation of o-aminohydroxy compounds with cyanoacetamides and — if desired — subsequent replacement of the amide grouping by different amide grouping or ester grouping.

The aldol condensation is, as known, carried out preferably in polar organic solvents, optionally containing water, in the presence of basic catalysts. Suitable solvents are: methanol, ethanol, n-propanol, isopropanol, n-butanol, ethylene glycol monomethyl ether, dioxane, formamide, dimethylformamide or dimethylsulphoxide.

Suitable basic catalytsts are: potassium carbonate, sodium acetate, potassium hydroxide, sodium ethylate or organic nitrogen bases such as diethylamine, indoline, and pyridine, but especially pyrrolidine or piperidine.

The reaction temperatures for the aldol condensation can be varied over a major range, for example between 0° and 160° C. In general, a complete reaction to give the corresponding alkol condensation products is already achieved in the range of 0° to 50° C.

The cyclisation of these aldol condensation products to give the coumarine compounds of the formula X can, in the case of starting from aldehydes of the formula XI in which $Z_3$ represents H, already be effected by heating for several hours in the original condensation medium — appropriately at the reflux temperature of the solvent used. The cyclisation reaction can be accelerated by adding an acid catalyst, such as hydrochloric acid, sulphuric acid, phosphoric acid, p-toluenesulphonic acid, oxalic acid, boric acid, boron trifluoride, zinc chloride or aluminium chloride. If on the other hand, aldehydes of the formula XI are used, in which $Z_3$ is alkyl, the cyclisation is carried out under the usual conditions of an ether splitting, for example with aluminium chloride, pyridine hydrochloride, hydriodic acid, hydrobromic acid or hydrogen chloride.

The post-sulphonation of the oxazolyl-comarines (X) which are free of sulphonic acid groups can be carried out according to customary processes, in sulphuric acid containing $SO_3$.

A particularly advantageous embodiment of the process claimed for the manufacture of the oxazolyl-coumarines X is characterised in that, using a one-pot reaction, a cyanoacetic ester of the formula

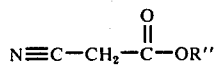

wherein
R'' represents a lower alkyl radical or benzyl radical, is first reacted, in a manner which is in itself known, with an amine of the formula

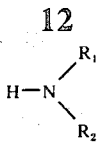

wherein
$R_1$ and $R_2$ independently of one another denote hydrogen, alkyl, cycloalkyl or aralkyl radicals, or together with the nitrogen atom, and optionally with the inclusion of further hetero-atoms as ring members, form a heterocyclic ring.

to give a cyanoacetic acid amide of the formula

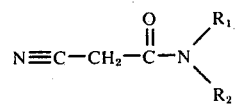

wherein
$R_1$ and $R_2$ have the abovementioned meaning,
that this compound is condensed, without intermediate isolation, with an o-amino-hydroxy compound of the formula II to give an oxazolyl-(2)-acetic acid amide of the formula I, and that this is in turn reacted, without intermediate isolation, with an aldehyde of the formula XI to give the compound of the formula X.

Another variant of the process described above for the manufacture of X consists of using sodium acetate as the basic catalyst and acetic anhydride as the solvent in accordance with the principle of the Perkin synthesis, starting from the free oxazolyl-acetic acids of the formula XII (B = OH).

Furthermore, the oxazolyl-coumarines of the formula X are obtained in a very smooth reaction if o-hydroxyaldehydes or o-alkoxyaldehydes of the formula XI and bis-oxazolyl-methanes of the formula

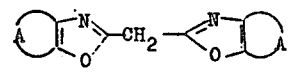 XIII in which
A has the abovementioned meanings,
are subjected to the aldol condensation, the cyclisation to give the coumarine is brought about, optionally after converting the o-alkoxy group into the hydroxyl group, and this coumarine is thereafter sulphonated, if desired, in the case where starting materials free of sulphonic acid groups are used.

If, for example, 4-diethylaminosalicylaldehyde and bis-benzoxazolyl-methane are used as the starting compounds, the reaction course, which must be described as extremely surprising, can be represented by the following set of equations:

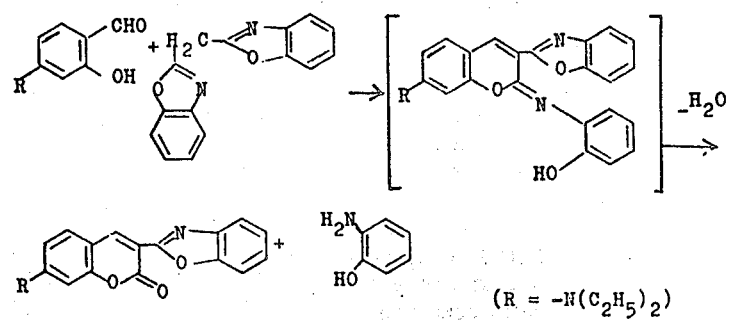

This aldol condensation is carried out completely analogously to the condensation of XI with XII explained above. As suitable bis-oxazolyl-methanes of the formula XIII there may for example be mentioned: bis-benzoxazolyl-methane, bis-(5-methylbenzoxazolyl)-methane, bis-(5,6-dimethyl-benzoxazolyl)-methane, bis-(5-chlorobenzoxazolyl)-methane, bis-(5,6-dimethyl-benzoxazolyl)-methane, bis-(5-chlorobenzoxazolyl)-methane, bis-(5-bromo-benzoxazolyl)-methane, bis-(5-fluoro-benzoxazolyl)-methane, bis-(5-ethylsulphonyl-benzoxazolyl)-methane, bis-(5-tertiary butylbenzoxazolyl)-methane, bis-(5-ethyl-benzoxazolyl)-methane, bis-(5-cyclohexyl-benzoxazolyl)-methane, bis-(5-phenyl-benzoxazolyl)-methane, bis-(6-methoxy-benzoxazolyl)-methane, bis-(5-benzyl-benzoxazolyl)-methane, bis-(5-dimethylaminosulphonyl-benzoxazolyl) methane, bis-(5-diethylaminocarbonyl-benzoxazolyl)-methane, bis-(5-ethoxy-benzoxazolyl)-methane, bis-(5-phenoxy-benzoxazolyl)-methane, bis-(5-acetylamino-benzoxazolyl)-methane, bis-naphth[2,3-d]oxazolyl-methane, bis-oxazolo[4,5-b]quinoxaline-methane, bis-(5,6-tetramethylene-benzoxazolyl)-methane and bis-(5,6-trimethylene-benzoxazolyl)-methane.

Amongst the abovementioned bis-oxazolyl-methanes, the unsubstituted compound is already known (Journal fur prakt. Chemie (4) 20 (1963), page 1 and thereafter). These compounds are obtained by heating o-amino-hydroxy compounds of the formula

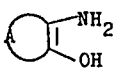 (II)

and a malonic acid diester, for example malonic acid diethyl ester, in the molar ratio of 2:1, appropriately in a high-boiling solvent, such as o-dichlorobenzene, whilst azeotropically distilling off the resulting alcohol and water through a column.

This last-mentioned process for the manufacture of oxazolyl-coumarines X can also be carried out, in a particularly advantageous embodiment, as a one-pot reaction by first condensing an o-aminohydroxy compound of the formula II with a malonic acid dialkyl ester, in the molar ratio of 2:1, to give a bis-oxazolyl-methane compound of the formula XIII, and then reacting this, without intermediate isolation, with an aldehyde of the formula XI. If this is carried out in an inert gas atmosphere, such as, for example, nitrogen, the o-amino-hydroxy compound of the formula II, liberated during the reaction, can be recovered from the mother liquor. In a further variant of the last-mentioned process for the manufacture of the new coumarines of the formula X, the procedure followed is to introduce the mixture of the starting components XI and XIII into concentrated sulphuric acid or phosphoric acid at room temperature and to pour out the resulting reaction mixture onto ice.

The new coumarine dyestuffs of the formula X are predominantly yellow to red crystalline powders which dissolve in organic media, especially solvents, such as alcohols, esters, amides, lower fatty acids, ethers and ketones, to give an intense yellow-green fluorescence. The coumarine dyestuffs of the formula X which contain sulphonic acid groups also dissolve in water, in which case, however, no fluorescence is observed.

The coumarine dyestuffs of the formula X are outstandingly suitable for dyeing oils and macromolecular organic materials, such as lacquers, films, foils, fibres and mouldings, for example those from cellulose esters, such as cellulose 2½-acetate and triacetate, polyvinyl compounds, such as polyvinyl chloride and polyvinyl acetate, polyolefines, such as polyethylene and polypropylene, polyamides, polyurethanes, polystyrene and polyesters, in bulk, in extremely brilliant, predominantly luminous yellow to orange shades. For this end use, the compounds of the formula X which are free of sulphonic acid groups, as well as those compounds containing sulphonic acid groups which are present as amine salts of alkylamines which confer liposolubility, can in particular be used.

These compounds can also be milled, together with organic pigments, especially yellow pigments, into the said materials, whereby a significant improvement in appearance is achieved.

A preferred field of use of the coumarine dyestuffs of the formula X, according to the invention, is the dyeing and printing of natural and synthetic fibre material and fabrics, especially those of wool, synthetic polyamides, polyurethanes and polyesters. Whilst the dyestuffs containing sulphonic acid groups are particularly suitable for dyeing polyamide, polyurethane and wool fibres, dyestuffs free of sulphonic acid groups give particularly good effects and fastness properties on polyester fibres and polyester fabrics.

The dyestuffs of the formula X, according to the invention, produce, on the said fibres and fabrics, extremely brilliant dyeings in yellow to orange shades, which fluoresce yellow-green in ultraviolet light and daylight, and which are distinguished by high colour strength, good build-up capacity and dyestuff uptake, and very good fastness properties, such as fastness to washing, rubbing, sublimation, perspiration, exhaust gases and light.

The compounds hitherto proposed as fluorescent yellow dyestuffs and orange dyestuffs do not possess these advantageous properties to the same extent. Compared to the nearest comparable 3-benzimidazolyl-coumarine dyestuff, known from German Published Specification No. 1,098,125 (and U.S. Pat. No. 3,458,380), the dyestuffs of the formula I, according to the invention, possess a higher brilliance, better dyestuff uptake and better light fastness on polyesters, as well as low sensitivity to changes in pH and better fastness to washing on polyamide. In comparison to the nearest comparable 3-benzthiazolyl-coumarine dyestuffs known from the German Published Specification quoted above, the better fastness to exhaust gas should be singled out.

The dyestuffs of the formula X, according to the invention, can be dyed and printed according to customary processes, for example in the form of aqueous solutions, dispersions or printing pastes. The dyebaths and printing pastes can contain the customary dyeing auxiliary additives, such as levelling agents, dispersing agents and dyeing accelerators, for example substituted polyglycol ethers, condensation products of aromatic sulphonic acids and formaldehyde, condensation products of higher molecular aliphatic amines and ethylene oxide, higher molecular alkylsulphates and alkylsulphonates in the form of their aqueous sodium salts or cyclohexylamine salts, condensation products of higher molecular alcohols and ethylene oxide, cellulose sulphite waste liquor products, o-hydroxydiphenyl, halogenated aromatic hydrocarbons and/or esters of aromatic carboxylic acids.

The dyestuffs according to the invention can also be dyed advantageously from organic solutions, for example of solutions in which solvents which are immiscible with water, such as tetrachloroethylene, trichloroethylene, 1,1,2-trichloroethane or 1,1,1-trichloropropane are used.

Unless otherwise stated, the parts stated in the examples which follow are parts by weight, and the temperature degrees stated are degrees centigrade.

EXAMPLE 1a 275 parts of technical o-aminophenol are mixed with 280 parts of cyanoacetamide and fused in a gentle stream of nitrogen. From 140° onwards, ammonia starts to be evolved strongly. The mixture is heated, whilst stirring, to 140° – 160° for 30 minutes, to 150° – 160° for 15 minutes and to 170° for 60 minutes. The melt is allowed to cool to 100°, 800 parts by volume of methanol are added, starting at 100°, whilst using reflux cooling, and the mixture is stirred, in a bath of ice, until cold. The crystalline precipitate formed is filtered off, washed with ice-cold methanol and dried at 50° in vacuo. 208 parts of the compound of the formula

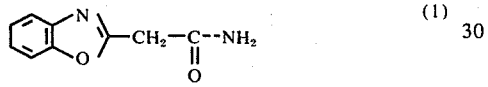

of melting point 187° – 189° are obtained. After recrystallisation from water (clarification with active charcoal) the substance melts at 190°.

Using the appropriate starting materials, the following compounds are manufactured analogously:

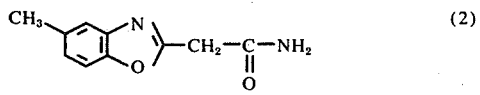

melting point 217° – 219°

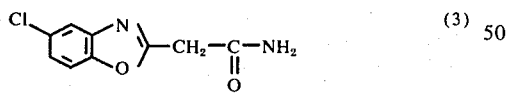

melting point 208° – 210°

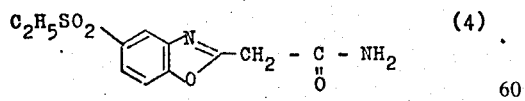

melting point 194°

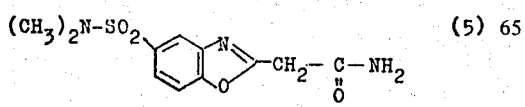

melting point 230° – 231°

The reaction of cyanoacetamide with 2-amino-4-bromophenol, 2-amino-4-methylsulphonyl-phenol, 2-amino-4-monoethylsulphonyl-phenol or 2-amino-4-diethylaminosulphonyl-phenol also takes place analogously.

EXAMPLE 2a 38 parts of 2-amino-4-cyclohexylphenol of melting point 166° – 169° and 33 parts of cyanoacetic acid cyclohexylamide of melting point 131° – 132° are mixed and fused in a gentle stream of nitrogen for 20 hours at 180°, during which time ammonia is evolved. The hot melt is then poured out and allowed to cool, whereupon it solidifies. After recrystallisation from 290 parts by volume of ethanol, 34.5 parts of compound of the formula

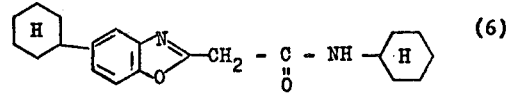

of melting point 169° – 170° are obtained.

The following compounds are manufactured analogously, using the appropriate starting materials:

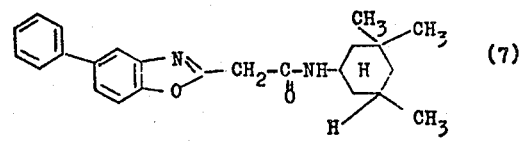

melting point 170.5° – 171.5°

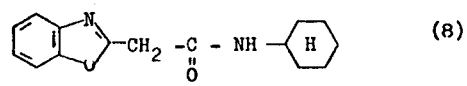

melting point 190° – 192°

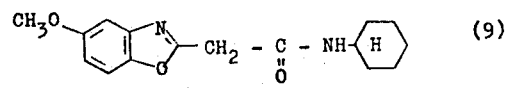

melting point 182° – 183°

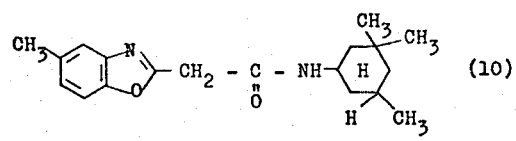

melting point 147° – 148°

EXAMPLE 3a 49 parts of cyanoacetic acid methylamide (melting point: 93° – 95°) and 79.5 parts of 1-amino-2-hydroxy-naphthalene are mixed and fused in a gentle stream of nitrogen for 15 hours at 180° – 190° bath temperature, in the course of which ammonia is evolved. The hot melt is then poured out and allowed to cool, whereupon it solidifies. After recrystallisation from 450 parts by volume of dimethylformamide, 36.5 parts of compound of the formula

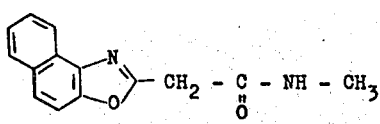 (11)

of melting point 195° – 197° are obtained.

The following compounds are manufactured analogously, using the appropriate starting materials:

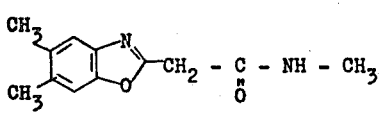 (12)

melting point 169° – 171°

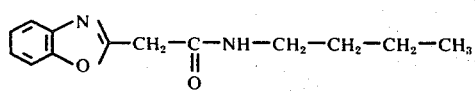  melting point 91 – 93°  (13)

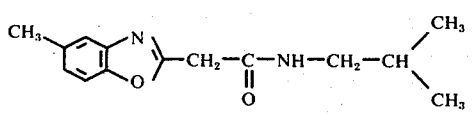  melting point 96 – 98°  (14)

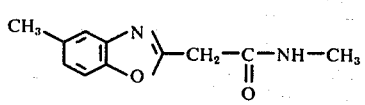  melting point 154 – 155°  (15)

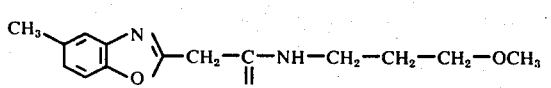  melting point 121 – 122.5°  (16)

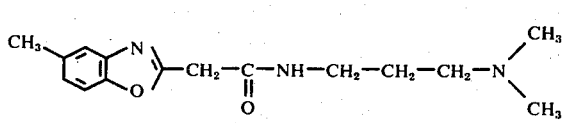  melting point 82 – 85°  (17)

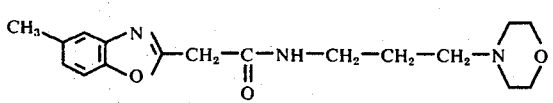  melting point 115 – 118°  (18)

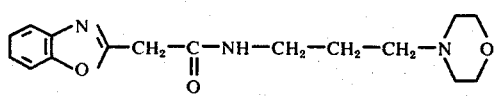  melting point 110 – 113°  (19)

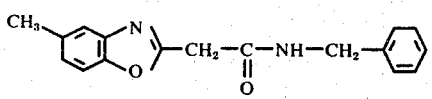  melting point 171.5 – 172.5°  (20)

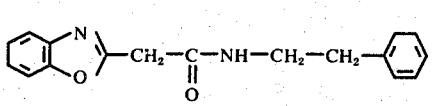  melting point 135 – 137°  (21)

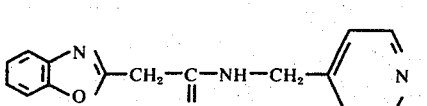  melting point 192 – 193°  (22)

The reaction of
1-amino-2-hydroxy-anthracene and cyanoacetic acid methylamide
5-amino-6-hydroxy-indane and cyanoacetic acid methylamide
4-amino-5-hydroxy-acenaphthene and cyanoacetic acid methylamide
o-aminophenol and cyanoacetic acid furfurylamide
o-aminophenol and cyanoacetic acid thenylamide
o-aminophenol and cyanoacetic acid sulpholane-3-amide
o-aminophenol and cyanoacetic acid tetrahydrofurfurylamide
o-aminophenol and cyanoacetic acid 2-N-(1',2',3'-triazolo)ethylamide
o-aminophenol and cyanoacetic acid 2-N-(1',2',4'-triazolo)ethylamide
o-aminophenol and cyanoacetic acid 3-N-(1',2',5'-triazolo)-n-propylamide
o-aminophenol and cyanoacetic acid 2-N-imidazoloethylamide
o-aminophenol and cyanoacetic acid 2-hydroxyethylamide
o-aminophenol and cyanoacetic acid 3-hydroxy-n-propylamide
o-aminophenol and cyanoacetic acid 3-n-butoxy-n-propylamide
o-aminophenol and cyanoacetic acid 3-chloro-n-propylamide
also takes place analogously.

EXAMPLE 4a 50 parts of cyanoacetic acid dodecylamide (melting point: 83° – 84°, from alcohol) and 26 parts of 2-amino-4-methyl-phenol (distilled in vacuo) are mixed and fused in a gentle stream of nitrogen for 18 hours at 180° – 190° bath temperature, in the course of which ammonia is evolved. The hot melt is then poured out and allowed to cool, whereupon it solidifies. Recrystallisation from 210 parts by volume of methylglycol yields 51.5 parts of the compound of the formula

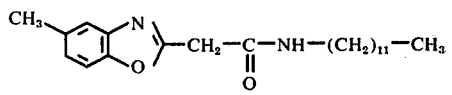  (23)

of melting point 98° – 100°. The following compounds are manufactured analogously, using the appropriate starting materials:

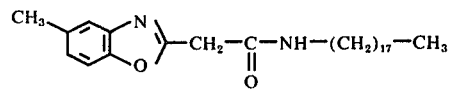

melting point 99 – 100°   (24)

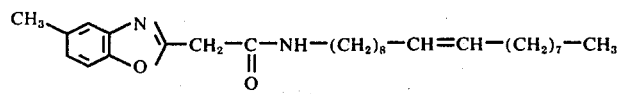

melting point 96 °   (25)

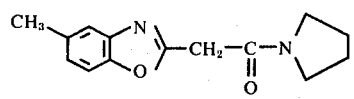   (26)

of melting point 86° – 89° are obtained. The following compounds are manufactured analogously, using the appropriate starting materials:

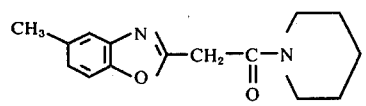

melting point 192 – 196°   (27)

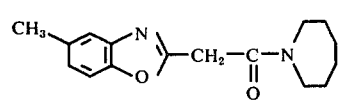

melting point 75 – 78°   (28)

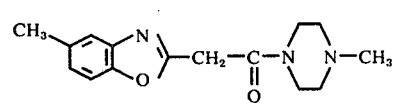

melting point 85 – 87°   (29)

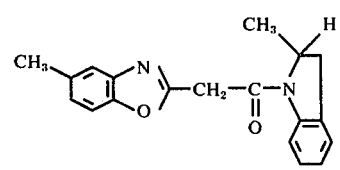

melting point 137 – 139°   (30)

The reaction of 2-amino-4-methyl-phenol with cyanoacetic acid aziridide, cyanoacetic acid morpholide, cyanoacetic acid thiomorpholide-S-dioxide, cyanoacetic acid N'-β-hydroxyethylpiperazide and cyanoacetyl-Δ²-pyrazoline also takes place analogously.

EXAMPLE 6a 40 parts of cyanoacetic acid anilide (melting point 196° – 198°) are mixed with 36 parts of 2-amino-4-methylphenol and fused in a gentle stream of nitrogen at 180° – 190° bath temperature for 15 hours, in the course of which ammonia is evolved. The hot melt is then poured out, whereupon it solidifies. After recrystallization from 100 parts by volume of n-butanol, 25 parts of the compound of the formula

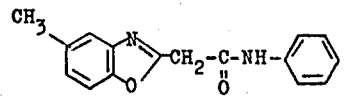   (31)

of melting point 165° – 166° are obtained. The following compounds are manufactured analogously using the appropriate starting materials:

EXAMPLE 5a 55 parts of cyanoacetic acid pyrrolidide (melting point: 69.5° – 70.5°) and 50 parts of 2-amino-4-methyl-phenol are heated in a gentle stream of nitrogen to 180° – 190° bath temperature for 12 hours, in the course of which ammonia is evolved. Thereafter the hot melt is taken up in 50 parts by volume of isopropanol and stirred with 250 parts by volume of petroleum ether at room temperature. The crystalline precipitate formed is filtered off, washed with petroleum ether and dried in vacuo at 40°.

75 parts of the compound of the formula

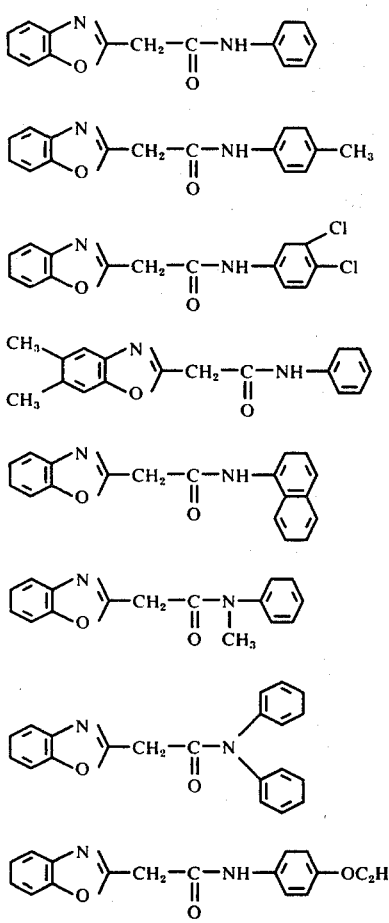

| | |
|---|---|
| melting point 154.5 – 155.5° | (32) |
| melting point 190 – 192° | (33) |
| melting point 155 – 157° | (34) |
| melting point 197 – 199° | (35) |
| melting point 198 – 200° | (36) |
| melting point 182 – 184° | (37) |
| melting point 210 – 212° | (38) |
| melting point 172 – 174° | (39) |

The reaction of cyanoacetic acid anilide with the following o-amino-hydroxy compounds is also carried out analogously: 2-amino-4-acetylamino-phenol, 2-amino-4-benzylphenol, 2-amino-4-benzylsulphonyl-phenol, 2-amino-4-phenylsulphonyl-phenol, 2-aminophenyl-4-carboxylic acid diethylamide, 2-amino-4-fluoro-phenol, 2-amino-4-(1',1',3',3'-tetramethyl)-butyl-phenol, 2-amino-4-β-methoxycarbonylethyl-phenol or 2-amino-4-phenoxy-phenol.

EXAMPLE 7a 33.6 parts of cyanoacetic acid dimethylamide (melting point: 58° – 61°) and 36.9 parts of 2-amino-4-methyl-phenol are mixed and fused in a gentle stream of nitrogen at 180° – 190° bath temperature for 10 hours, in the course of which ammonia is evolved. After cooling, the solidified melt cake is recyrstallized from 130 parts by volume of ethanol. 27 parts of the compound of the formula

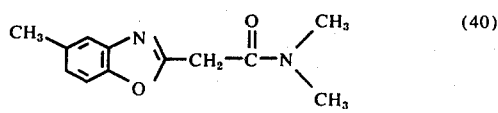 (40)

of melting point 90° – 91° are obtained.

The reaction of 2-aminophenol with the following cyanoacetamides is carried out analogously: cyanoacetic acid diethylamide, cyanoacetic acid di-n-butylamide, cyanoacetic acid dicyclohexylamide, cyanoacetic acid dibenzylamide, cyanoacetic acid N-methyl-ethanolamide and cyanoacetic acid N-methyl-N-(3-aminopropyl)-ethanolamide.

EXAMPLE 8a 45.2 parts of cyanoacetic acid ethyl ester are stirred with 36 parts of 3-methoxypropylamine, in the course of which the temperature is prevented from rising above 60° by gentle cooling. The mixture is subsequently warmed to 60° for a further hour, then mixed with 48 parts of 2-amino-4-methylphenol under nitrogen, and the mixture heated in a gentle stream of nitrogen to 180° – 185° bath temperature over the course of 30 minutes, whilst distilling off liquid, and warmed for a further 5 hours to 180° bath temperature, in the course of which ammonia is evolved. The hot melt is then poured out and allowed to cool, whereupon it solidifies. Recrystallizaton from 230 parts by volume of benzene yields 63 parts of the compound of the formula (16) of melting point 121° – 122.5°.

The compounds of the formulae (1) to (15) and (17) to (42) can also be manufactured analogously, using the appropriate starting materials, and instead of cyanoacetic acid ethyl ester equivalent amounts of cyanoacetic acid methyl ester or of other cyanoacetic acid esters derived from lower aliphatic alcohols, such as are used in Example 12, or cyanoacetic acid benzyl ester, can be employed with equal success.

EXAMPLE 9a 19 parts of bis-cyanoacetic acid ethylenediamide and 25 parts of 2-amino-4-methyl-phenol are mixed and fused in a gentle stream of nitrogen at 180° bath temperature, in the course of which ammonia is evolved. After about 2 hours the melt solidifies to crystals. It is nevertheless heated to 180° for 10 hours, cooled to 100°, dissolved in 130 parts by volume of hot dimethylformamide, and the solution cooled. The resulting crystalline precipitate is filtered off, washed with alcohol and dried in vacuo at 80°. 12 parts of the compound of the formula ing point: 158° – 159°), manufactured by coupling sulphanilic acid with 2-hydroxydibenzofurane in alkaline solution, neutralising, isolating the resulting azo dyestuff and subsequently reducing it in hot aqueous solution by means of sodium hydrosulphite, and 6 parts of cyanoacetic acid anilide, are fused in a gentle stream of nitrogen for 19 hours at 180°. The hot melt is then poured out, whereupon it solidifies. Recrystallisation from 25 parts of methylglycol yields 3.5 parts of the

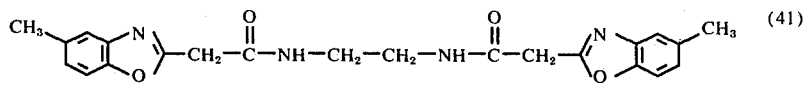
(41)

of melting point 254° – 256° are obtained.

The reaction of o-aminophenol with the following components is carried out analogously: bis-cyanoacetic acid piperazide, bis-cyanoacetic acid 1,4-dicyclohexylamide, bis-cyanoacetic acid p-phenylenediamide and bis-cyanoacetic acid 4,4'-(diphenylmethane)-diamide.

EXAMPLE 10a 7 parts of the compound of the formula (1) and 6 parts of cyclohexylamine in 40 parts by volume of n-amyl alcohol are heated to the boil for 20 hours under reflux, in the course of which ammonia is evolved, and are subseqently cooled. The resulting crystalline precipitate is filtered off, washed with ice-cold methanol and dried in vacuo at 50°. 8.5 parts of the compound of the formula (8) (see Example 2a !) of melting point 190° – 192° are obtained.

The following compounds are reacted analogously: compound (1) and 3,4-dichloroaniline (reaction time: 40 hours) to give compound (34), compound (1) and β-phenylethylamine (reaction time: 24 hours) to give compound (21), compound (1) and p-toluidine (reaction time: 48 hours) to give compound (33), compound (15) and benzylamine (reaction time: 20 hours) to give compound (20), compound (15) and isophorylamine (reaction time: 25 hours) to give compound (10), compound (15) and 2-amino-4-methyl-phenol (reaction time: 50 hours) to give compound (43), compound (15) and 2-methylindoline (reaction time: 60 hours under nitrogen) to give compound (30), and compound (15) and n-dodecylamine (reaction time: 30 hours) to give compound (23).

The following components can also be reacted analogously: compound (11) and cyclohexylamine (24 hours), compound (12) and 3-(N-morpholino)-n-propylamine (32 hours), compound (2) and 4-bromoaniline (48 hours), compound (40) and 1-amino-naphthalene (50 hours), compound (40) and 4-picolylamine (30 hours), compound (15) and dicyclohexylamine (48 hours), and compound (1) and diphenylamine (60 hours).

EXAMPLE 11a 7.5 parts of 1-amino-2-hydroxy-dibenzofurane (melt-compound of the formula

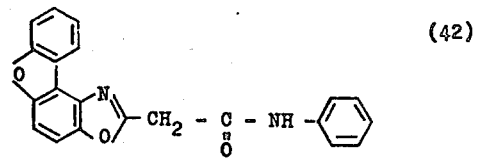
(42)

of melting point 216° – 218°.

The following components are reacted analogously: 3-amino-4-hydroxy-pyridine and cyanoacetic acid methylamide, 7-amino-8-hydroxy-quinoline and cyanoacetic acid cyclohexylamide, 3-amino-2-hydroxy-quinoxaline and cyanoacetic acid propylamide, 5-amino-1,3-dimethyl-barbituric acid and cyanoacetic acid methylamide, and 1-ethyl-6-hydroxy-7-aminoindazole and cyanoacetic acid methylamide.

EXAMPLE 12a 240 parts of 2-amino-4-methyl-phenol (technical grade) and 280 parts of cyanoacetic acid ethyl ester are heated in a gentle stream of nitrogen to 160° – 170° for 2.5 hours, whilst stirring and allowing liquid to distil off. Thereafter 60 parts by volume of dimethylformamide are added, starting at 140°, and 840 parts by volume of methanol are added, starting at 100° and using reflux cooling, and the mixture is left to stir in a bath of ice until cold. The resulting crystalline precipitate is filtered off, washed with ice-cold methanol and dried at 60° in vacuo. 96 parts of the compound of the formula

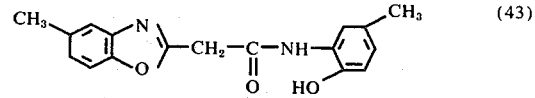
(43)

of melting point 219° – 221° are obtained. A sample (5 parts) recrystallised from methylglycol (65 parts by volume) melts at 223° – 224°.

The following substances are reacted analogously: Cyanoacetic acid benzyl ester and o-aminophenol to give

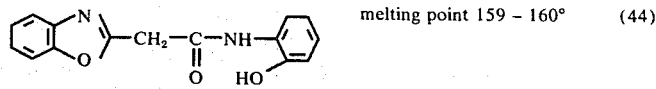
melting point 159 – 160°  (44)

Cyanoacetic acid methoxyethyl ester and 2-amino-4-tert.butylphenol (melting point 159° – 162°) to give

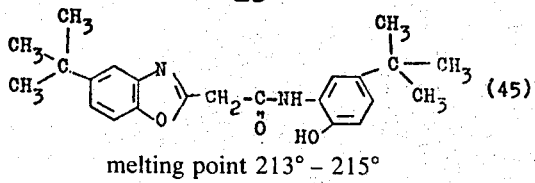

melting point 213° – 215°

Cyanoacetic acid methyl ester and 2-amino-4-chlorophenol to give

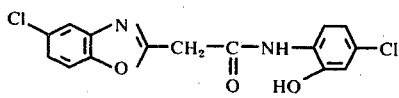   melting point 227 – 228°   (46)

Cyanoacetic acid n-propyl ester and 2-amino-4-dimethylaminosulphonyl-phenol, at 200°, to give

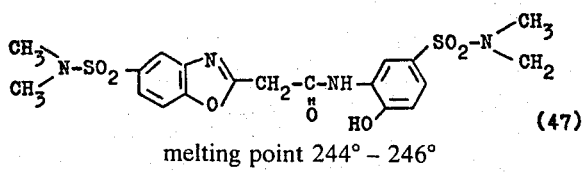

melting point 244° – 246°

Cyanoacetic acid ethyl ester can, furthermore, be reacted analogously, in a molar ratio of 1:2, with the following components: 2-amino-4-cyclohexylphenol (at 170° – 180°), 2-amino-4-phenyl-phenol (at 180° – 185°), 2-amino-3,5-dimethylphenol (at 170°), 2-amino-4-benzylphenol (at 180°), 2-amino-4-ethoxy-phenol (at 160° – 170°), 1,-amino-2-hydroxy-naphthalene (at 180°) and 3-amino-4-hydroxy-quinoline (at 170° – 180°).

EXAMPLE 1b 22.6 parts of cyanoacetic acid ethyl ester and 18 parts of 3-methoxy-propylamine are mixed whilst cooling and are warmed to 60° for 30 minutes. Thereafter, 25 parts of 3-amino-4-hydroxy-toluene are added. The mixture is heated to 180° (bath temperature) under nitrogen, in the course of which liquid is allowed to distil off. On cooling, the melt solidifies to crystals. The compound thus obtained, of the formula

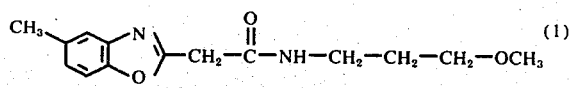

is mixed, without intermediate isolation, with 38.5 parts of 4-diethylamino-salicylaldehyde, 300 parts by volume of isopropanol and 2 parts by volume of piperidine and is heated for 20 hours to the boil under reflux, whilst stirring. After cooling to 5°, the crystalline precipitate is filtered off, washed with ice-cold alcohol and dried at 70° in vacuo. 33.7 parts of the compound of the formula

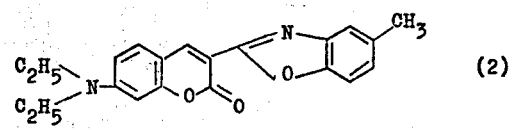

of melting point 204° – 206° are obtained.

The same result is achieved if instead of cyanoacetic acid ethyl ester an equivalent amount of cyanoacetic acid methyl ester, n-propyl ester, isopropyl ester, isobutyl ester of benzyl ester is employed, of if, instead of 3-methoxy-propylamine, an equivalent amount of n-propylamine, n-butylamine, dimethylamine (in the form of a 30% strength aqueous solution), pyrrolidine or piperidine is employed.

Using the same process and employing 4-dimethylaminosalicylaldehyde, the compound of the formula

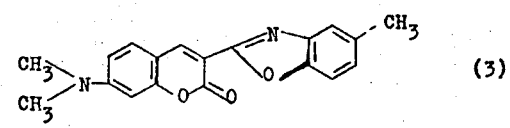

of melting point 279° – 281° is obtained, whilst on employing o-aminophenol instead of 3-amino-4-hydroxy-toluene the compound of the formula

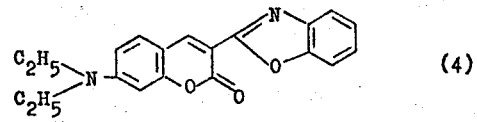

of melting point 184.5° – 185.5° is obtained.

Again using the same process and employing the salicylaldehydes indicated in the Table below, the compounds of the formula

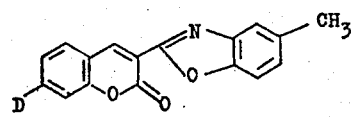

are obtained:

Table

| Salicylaldehyde of the formula II | D | Compound No. | Colour shade |
|---|---|---|---|
| 4-β-cyanoethyl-methylamino-salicylaldehyde | NC—CH₂—CH₂—N(CH₃)— | (5) | greenish-tinged yellow |
| 4-di-n-butylamino-salicylaldehyde | (CH₃—CH₂—CH₂—CH₂)₂N— | (6) | greenish-tinged yellow |

Table-continued

| Salicylaldehyde of the formula II | D | Compound No. | Colour shade |
|---|---|---|---|
| 4-benzyl-methylamino-salicylaldehyde | C$_6$H$_5$—CH$_2$—N(CH$_3$)— | (7) | greenish-tinged yellow |
| 4-dibenzylamino-salicylaldehyde | (C$_6$H$_5$—CH$_2$)$_2$N— | (8) | greenish-tinged yellow |
| 4-β-phenylethylamino-salicylaldehyde | C$_6$H$_5$—CH$_2$—CH$_2$—NH— | (9) | greenish-tinged yellow |
| 4-β-methoxyethyl-methylamino-salicylaldehyde | CH$_3$O—CH$_2$—CH$_2$—N(CH$_3$)— | (10) | greenish-tinged yellow |
| 4-hydroxyethyl-ethylamino-salicylaldehyde | HO—CH$_2$—CH$_2$—N(CH$_2$CH$_3$)— | (11) | greenish-tinged yellow |
| 4-n-propylamino-salicylaldehyde | CH$_3$—CH$_2$—CH$_2$—NH— | (12) | greenish-tinged yellow |
| 4-β-chloroethyl-methylamino-salicylaldehye | Cl—CH$_2$—CH$_2$—N(CH$_3$)— | (13) | greenish-tinged yellow |
| 4-di-n-propylamino-salicylaldehyde | (CH$_3$—CH$_2$—CH$_2$)$_2$N— | (14) | greenish-tinged yellow |
| 4-bromoethylamino-salicylaldehyde | Br—CH$_2$—CH$_2$—NH— | (15) | greenish-tinged yellow |
| 4-β-acetoxyethylamino-salicylaldehyde | CH$_3$—C(=O)—O—CH$_2$—CH$_2$—NH— | (16) | greenish-tinged yellow |
| 4-β-acetylethylamino-salicylaldehyde | CH$_3$—C(=O)—CH$_2$—CH$_2$—NH— | (17) | greenish-tinged yellow |
| 4-cyclopentylamino-salicylaldehyde | cyclopentyl-CH(H)—NH— | (18) | greenish-tinged yellow |
| 4-N-pyrrolidyl-salicylaldehyde | (pyrrolidin-1-yl)— | (19) | greenish-tinged yellow |
| 4-N-piperidyl-salicylaldehyde | (piperidin-1-yl)— | (20) | greenish-tinged yellow |
| 4-N-morpholinyl-salicylaldehyde | (morpholin-4-yl)— | (21) | greenish-tinged yellow |
| 4-N-(N'-methyl-piperazyl)-salicylaldehyde | CH$_3$—N(piperazin-1-yl)— | (22) | greenish-tinged yellow |
| 4-N-(phenylpyrazolinyl)-salicylaldehyde | (5-phenyl-2-pyrazolin-1-yl)— | (23) | greenish-tinged yellow |
| 4-N-indolinyl-salicylaldehyde | (indolin-1-yl)— | (24) | greenish-tinged yellow |

Table-continued

| Salicylaldehyde of the formula II | D | Compound No. | Colour shade |
|---|---|---|---|
| 4-isobutylamino-salicylaldehyde | $\begin{array}{c}CH_3\\ \phantom{CH_3}\diagdown\\ \phantom{CH_3}CH-CH_2-N-\\ \phantom{CH_3}\diagup\phantom{CH-CH_2-N-}H\\ CH_3\end{array}$ | (25) | greenish-tinged yellow |
| 4-di-hexylamino-salicylaldehyde | $[CH_3(CH_2)_5]_2N-$ | (26) | greenish-tinged yellow |
| 4-n-dodecylamino-salicylaldehyde | $CH_3-(CH_2)_{11}-\underset{H}{N}-$ | (27) | greenish-tinged yellow |
| 4-n-stearylamino-salicylaldehyde | $CH_3-(CH_2)_{17}-\underset{H}{N}-$ | (28) | greenish-tinged yellow |
| 4-allyl-methylamino-salicylaldehyde | $CH_2=CH-CH_2-\underset{\underset{CH_3}{\mid}}{N}-$ | (29) | greenish-tinged yellow |

EXAMPLE 2b 15 parts of the compound of the formula

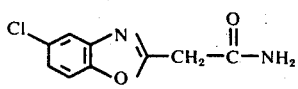  (30)

of melting point 201° – 202°, 14 parts of 4-diethylaminosalicylaldehyde, 200 parts by volume of ethanol and 1 part by volume of piperidine are heated to the boil, under reflux and whilst stirring, for 23 hours, in the course of which ammonia is evolved, and are then cooled to 10°. The resulting crystalline precipitate is filtered off, washed with ice-cold alcohol and dried in vacuo at 60°. 26 parts of the compound of the formula

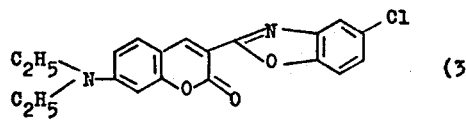  (31)

of melting point 202° – 204° (from dimethylformamide) are obtained.

If instead of compound (30) an equivalent quantity of 5-dimethylaminosulphonyl-benzoxazolyl-(2)-acetamide (melting point 230° – 231°) is employed, the compound of the formula

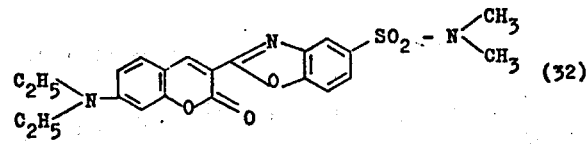  (32)

of melting point 223° – 225° is obtained analogously.

If instead of compound (30) an equivalent quantity of 5-ethylsulphonyl-benzoxazolyl-(2)-acetamide (melting point 194°) is employed, the compound of the formula

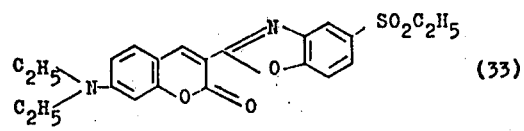  (33)

of melting point 186° – 188° (from chlorobenzene) is obtained analogously.

Using the appropriate benzoxazolyl-(2)-acetamides, the compounds of the formula

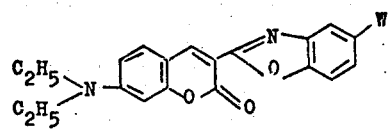

listed in the Table which follows, are again manufactured in an analogous manner.

Table

| Benzoxazolyl-(2)-acetamide | W | Compound No. | Colour shade |
|---|---|---|---|
| 5-phenylsulphonyl-benzoxazolyl-(2)-acetamide | $-SO_2-\phantom{}\bigcirc$ | (34) | greenish-tinged yellow |
| 5-bromoethyl-benzoxazolyl-(2)-acetamide | $-CH_2-CH_2-Br$ | (35) | greenish-tinged yellow |
| 5-methoxy-benzoxazolyl-(2)-acetamide | $-OCH_3$ | (36) | yellow |
| 5-acetylamino-benzoxazolyl-(2)-acetamide | $-NH-\underset{\underset{}{\overset{\overset{O}{\|}}{C}}}-CH_3$ | (37) | yellow |
| 5-benzenesulphonylamino-benzoxazolyl-(2)-acetamide | $-NH-SO_2-\bigcirc$ | (38) | yellow |

Table-continued

| Benzoxazolyl-(2)-acetamide | W | Compound No. | Colour shade |
|---|---|---|---|
| 5-β-hydroxyethyl-benzoxazolyl-(2)-acetamide | $-CH_2-CH_2-OH$ | (39) | greenish-tinged yellow |
| 5-benzyl-benzoxazolyl-(2)-acetamide | $-CH_2-\langle\mathrm{C_6H_5}\rangle$ | (40) | greenish-tinged yellow |

EXAMPLE 3b 12 parts of the compound of the formula

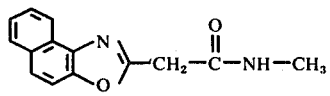

(41)

of melting point 195° – 197°, 9.7 parts of 4-diethylamino-salicylaldehyde, 90 parts by volume of ethanol and 0.3 part by volume of pyrrolidine are heated to the boil, under reflux and whilst stirring, for 20 hours, in the course of which methylene is evolved, and are then cooled to 10°. The resulting crystalline precipitate is filtered off, washed with methanol and dried in vacuo at 70°. 14.5 parts of the compound of the formula

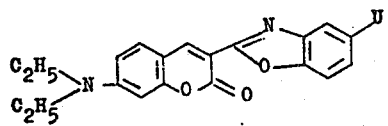

which after recrystallization from toluene melts at 198° – 200° C, are obtained. Compound (42) is obtained in the same manner if instead of naphth[1,2-d]oxazolyl-(2)-acetic acid methylamide (41) the dimethylamide, pyrrolidide, piperidide, anilide or p-toluidide of the same acid is employed.

The compounds of the formula listed in the Table which follows are manufactured analogously, using the appropriate benzoxazolyl-(2)-acetic acid methylamides:

Table

| Benzoxazolyl-(2)-acetic acid methylamides | U | Compound No. | Colour shade |
|---|---|---|---|
| 5-benzylsulphonyl-benzoxazolyl-(2)-acetic acid methylamide | $\langle C_6H_5\rangle-CH_2-SO_2-$ | (43) | greenish-tinged yellow |
| 5-ethoxy-benzoxazolyl-(2)-acetic acid methylamide | $C_2H_5O-$ | (44) | yellow |
| 5-methylaminosulphonyl-benzoxazolyl-(2)-acetic acid methylamide | $CH_3-NH-SO_2-$ | (45) | greenish-tinged yellow |
| 5-diethylaminocarbonyl-benzoxazolyl-(2)-acetic acid methylamide | $\begin{array}{c}C_2H_5\\ \phantom{C_2H_5}\diagdown\\ \phantom{C_2H_5}N-CO-\\ \phantom{C_2H_5}\diagup\\ C_2H_5\end{array}$ | (46) | greenish-tinged yellow |
| 5-n-propylaminocarbonyl-benzoxazolyl-(2)-acetic acid methylamide | $CH_3-CH_2-CH_2-NH-CO-$ | (47) | greenish-tinged yellow |
| 5-β-chloroethyl-benzoxazolyl-(2)-acetic acid methylamide | $Cl-CH_2-CH_2-$ | (48) | greenish-tinged yellow |
| 5-β-methoxyethylbenzoxazolyl-(2)-acetic acid methylamide | $CH_3O-CH_2-CH_2-$ | (49) | greenish-tinged yellow |
| 5-phenoxy-benzoxazolyl-(2)-acetic acid methylamide | $\langle C_6H_5\rangle-O-$ | (50) | yellow |
| 5-n-propyl-benzoxazolyl-(2)-acetic acid methylamide | $CH_3-CH_2-CH_2-$ | (51) | greenish-tinged yellow |

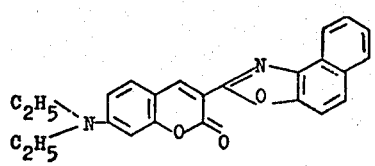

(42)

The compounds listed in the Table which follows are again manufactured analogously, using the appropriate oxazolyl-(2)-acetic acid methylamides:

Table

| Oxazolyl-(2)-acetic acid methylamides | Coumarine compounds of the formula 1 | Compound No. | Colour shade |
|---|---|---|---|
| 4,5-tetramethylene-benzoxazolyl-(2)-acetic acid methylamide | | (52) | greenish-tinged yellow |
| 5,6-trimethylene-benzoxazolyl-(2)-acetic acid methylamide | | (53) | greenish-tinged yellow |
| 5,6-dimethyl-benzoxazolyl-(2)-acetic acid methylamide | | (54) | greenish-tinged yellow |
| 5-methyl-benzoxazolyl-(2)-acetic acid methylamide-6-sulphonic acid | | (55) | greenish-tinged yellow |
| naphth[1,2-d]oxazolyl-(2)-acetic acid methylamide-disulphonic acid | | (56) | yellow |

When manufacturing the acid compounds (55) and (56) it is advisable to increase the amount of pyrrolidine to the point that in these cases, also, the reaction medium is alkaline.

The following oxazolyl-(2)-acetic acid methylamides can also be reacted analogously with 4-diethylamino-salicylaldehyde to give corresponding coumarine dyestuffs:

| | Colour of the coumarine: |
|---|---|
| anthra[2,1-d]oxazolyl-(2)-acetic acid methylamide | orange |
| phenanthreno[9,10-d]oxazolyl-(2)-acetic acid methylamide | orange |
| fluoreno[2,3-d]oxazolyl-(2)-acetic acid methylamide | orange |
| acenaphth[5,4-d]oxazolyl-(8)-acetic acid methylamide | orange |

EXAMPLE 4b 10.2 parts of the compound of the formula

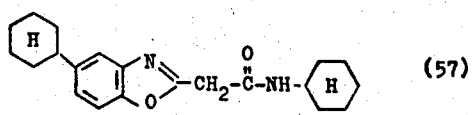

(57)

of melting point 169° – 170°, 5.8 parts of 4-diethylamino-salicylaldehyde, 110 parts by volume of ethanol and 0.5 part by volume of piperidine are heated to the boil for 20 hours, under reflux and whilst stirring. After cooling to 10°, the resulting crystalline precipitate is filtered off, washed with ice-cold alcohol and dried at 60° in vacuo.

6.6 parts of the compound of the formula melting at 167° – 169° after recrystallisation from dimethylformamide, are obtained.

If 4-diethylaminosalicylaldehyde, instead of being reacted with the compound (57), is reacted with the equivalent quantity of 5-tertiary butyl-benzoxazolyl-(2)-acetic acid cyclohexylamide, the compound of the formula (59)

of melting point 244° – 245° (from dimethylformamide) is obtained analogously.

EXAMPLE 5b 11.3 parts of the compound of the formula (60)

of melting point 170° – 171.5°, 5.8 parts of 4-diethylaminosalicylaldehyde, 60 parts by volume of ethanol and 0.2 part by volume of piperidine are heated to the boil for 20 hours under reflux and whilst stirring, and are then cooled to 10°. The crystalline precipitate is filtered off, washed with alcohol and recrystallised from methylglycol. 6.1 parts of the compound of the formula (61)

of melting point 184° – 186° are obtained.

EXAMPLE 6b 13 parts of the compound of the formula (62)

of melting point 197° – 199°, 8 parts of 4-dimethylaminosalicylaldehyde, 400 parts by volume of ethanol and 2 parts by volume of pyrrolidine are heated to the boil for 20 hours, under reflux and whilst stirring, and are then cooled to 10°. The resulting crystalline precipitate is washed with ice-cold methanol and dried in vacuo at 80°. 13.5 parts of the compound of the formula of melting point 306° – 308° (from chlorobenzene) are obtained.

The following compounds are manufactured analogously, using the appropriate benzoxazolyl-(2)-acetanilides:

from 5-(1',1',3',3'-tetramethyl-n-butyl)-benzoxazolyl-(2)-acetanilide (64)

from 5-fluoro-benzoxazolyl-(2)-acetanilide (65)

EXAMPLE 7b 67 parts of the compound of the formula (66)

of melting point 158° – 159°, 48 parts of 4-diethylaminosalicylaldehyde, 1000 parts by volume of ethanol and 5 parts by volume of piperidine are heated to the boil for 24 hours, under reflux and whilst stirring, and are then cooled. The resulting crystalline precipitate is filtered off, washed with ice-cold methanol and dried in vacuo at 60°. 76 parts of the compound of the formula (67)

are obtained, melting, after recrystallisation from methylglycol, at 184.5° – 185.5° (compare with the compound of the formula (4) in Example 1b !).

The compound of the formula (68)

of melting point 304° – 306° (from dimethylformamide) is manufactured analogously from compound (66) and 4-dimethylaminosalicylaldehyde. Using 4-dimethylamino-5-methyl-salicylaldehyde, the compound of the formula

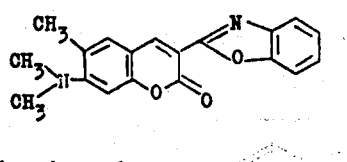

(69)

is produced analogously.

If, in the instruction given above, the compound (66) is replaced by equivalent quantities of substituted benzoxazolyl-(2)-acetic acid 2'-hydroxy-anilides, the compounds indicated in the Table which follows are obtained analogously:

of melting point 216° – 218°, 13.3 parts of 4-diethylaminosalicylaldehyde, 300 parts by volume of ethanol and 1 part by volume of piperidine are heated to the boil for 22 hours under reflux and whilst stirring and are then cooled. The crystalline precipitate is filtered off, washed with methanol and dried at 70° in vacuo. 30 parts of the compound of the formula

| Benzoxazolyl-(2)-acetic acid 2'-hydroxy-anilide | Coumarine compound | Compound No. | Colour shade |
|---|---|---|---|
| 5-isopropyl-benzoxazolyl-(2)-acetic acid 2'-hydroxy-5'-isopropyl-anilide | | (70) | greenish-tinged yellow |
| 5-bromo-benzoxazolyl-(2)-acetic acid 2'-hydroxy-5'-bromo-anilide | | (71) | greenish-tinged yellow |
| 5-ethyl-benzoxazolyl-(2)-acetic acid 2'-hydroxy-5'-ethyl-anilide | | (72) | greenish-tinged yellow |

EXAMPLE 6b 24 parts of the compound of the formula

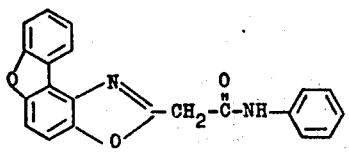

(73)

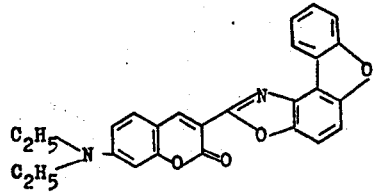

(74)

melting at 285° – 287° after recrystallization from benzene, are obtained.

The coumarine dyestuffs indicated in the Table which follows are manufactured analogously from 4-diethylaminosalicylaldehyde and the appropriate heterocyclically fused oxazolyl-(2)-acetanilides:

Table

| Acetanilides | Coumarine Dyestuffs | Compound No. | Colour Shade |
|---|---|---|---|
| Oxazolo[5,4-b]pyridine-(2)-acetanilide | | (75) | greenish-tinged yellow |

Table-continued

| Acetanilides | Coumarine Dyestuffs | Compound No. | Colour Shade |
|---|---|---|---|
| Oxazolo[4,5-g]quinoline-(2)-acetanilide | | (76) | yellow |
| Oxazolo[4,5-c]quinoline-(2)-acetanilide | | (77) | yellow |
| Oxazolo[5,4-d]pyrimidine-(2)-acetanilide | | (78) | greenish-tinged yellow |
| Oxazolo[4,5-d]pyridazine-(2)-acetanilide | | (79) | greenish-tinged yellow |
| Oxazolo[4,5-b]quinoxaline-(2)-acetanilide | | (80) | yellow |
| Oxazolo[4,5-b]phenazine-(2)-acetanilide | | (81) | orange |
| 5H-Oxazolo[4,5-b]phenoxazine-acetanilide | | (82) | orange |

EXAMPLE 9b 20.4 parts of the compound of the formula

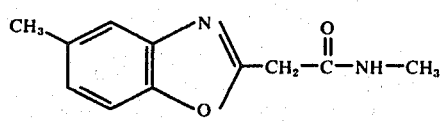
(83)

of melting point 154° – 155°, 22.1 parts of 4-diethylamino-2ethoxy-benzaldehyde, 220 parts by volume of ethanol and 1 part by volume of piperidine are heated to the boil for 12 hours under reflux and whilst stirring, and are then cooled to 10°. The solvent is distilled off on a waterbath (finally in vacuo). 40 parts of the compound of the formula

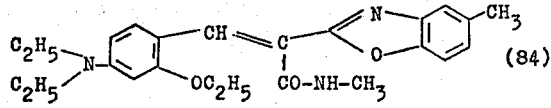
(84)

of melting point 179° – 181° (alcohol) are obtained as the residue. 22 parts of ths compound are suspended in 120 parts by volume of anhydrous benzene, treated with 34 parts of anhydrous aluminium chloride, and subsequently heated to the boil for 24 hours. The reaction mixture is poured out onto 25 parts by volume of 30% strength hydrochloric acid and 25 parts of ice and the benzene is then distilled off azeotropically. The crystalline precipitate is filtered off and washed with water. 20 parts of compound of the formula (2), of melting point 204° – 206° (from dimethylformamide) are obtained.

If, in the above instruction 4-diethylamino-2-ethoxybenzaldehyde is replaced by equivalent quantities of the following 2-alkoxy-benzaldehyde, the coumarine dyestuffs listed in the Table below are obtained analogously:

The same compound is obtained if instead of the compound of the formula (83), an equivalent quantity of one of the following 5-methyl-benzoxazolyl-(2)-acetic acid amides is employed: 5-methyl-benzoxazolyl-(2)-acetic acid diethylamide, 5-methyl-benzoxazolyl-(2)-acetic acid di-n-butylamide, 5-methyl-benzoxazolyl-(2)-acetic acid pyrrolidide, 5-methylbenzoxazolyl-(2)-acetic acid piperidide, 5-methyl-benzoxazolyl(2)-acetic acid morpholide, 5-methyl-benzoxazolyl-(2)-acetic acid-(2) azepide, 5-methyl-benzoxazolyl-(2)-acetic acid aziridide, 5-methyl-benzoxazolyl-(2)-acetic acid N'-methylpiperazide, 5-methyl-benzoxazolyl-(2)-acetic acid N-methylanilide, 5-methyl-benzoxazolyl-(2)-acetic acid tetrahydrofurfurylamide, 5-methyl-benzoxazolyl-(2)-acetic acid furfurylamide, 5-methyl-benzoxazolyl-(2)-acetic acid thenylamide, 5-methyl-benzoxazolyl-(2)-acetic acid benzylamide, Table

| 2-Alkoxybenzaldehyde | Coumarine Dyestuff | Compound No. | Colour Shade |
|---|---|---|---|
| 4-β-Cyamomethyl-methylamino-2-methoxy-benzaldehyde | | (5) | greenish-tinged yellow |
| 4-Hexahydrobenzyl-methylamino-2-methoxy-benzaldehyde | | (85) | greenish-tinged yellow |
| 4-Cyclohexylamino-2-methoxy-benzaldehyde | | (86) | greenish-tinged yellow |
| 4-Diethylamino-2-ethoxy-benzaldehyde-5-sulphonic acid | | (87) | greenish-tinged yellow |

EXAMPLE 10b 20.4 parts of the compound of the formula (83), 19.5 parts of 4-diethylamino-salicylaldehyde, 250 parts by volume of ethanol and 2 parts by volume of piperidine are heated to the boil for 18 hours under reflux and whilst stirring, and are then cooled to 15°. The crystalline precipitate is filtered off, washed with alcohol and dried in vacuo at 60°. 31.2 parts of the compound of the formula (2), of melting point 204°–206° (compare Example 1b) are obtained.

5-methylbenzoxazolyl-(2)-acetic acid β-phenylethylamide, 5-methylbenzoxazolyl-(2)-acetic acid 4'-picolylamide, 5-methyl-benzoxazolyl-(2)-acetic acid 2'-hydroxyethylamide, 5-methyl-benzoxazolyl-(2)-acetic acid 3'-dimethylamino-n-propylamide, 5-methyl-benzoxazolyl-(2)-acetic acid 3'-morpholino-n-propylamide, 5-methyl-benzoxazolyl-(2)-acetic acid 2'-bromoethylamide, 5-methyl-benzoxazolyl-(2)-acetic acid n-butylamide, 5-methylbenzoxazolyl-(2)-acetic acid n-hexylamide, 5-methyl-benzoxazolyl(2-acetic acid p-toluidide, 5-methyl-benzoxazolyl-(2)- acetic acid phenetidide and 5-methyl-benzoxazolyl-(2)-acetic acid 1'-naphthylamide.

EXAMPLE 11b 24 parts of compound of the formula (2) are gradually introduced into 150 parts of sulphuric acid (density: 1.85) whilst cooling and stirring, and the whole is stirred for 15 minutes at 20° – 25°. When all has dissolved, 60 parts of oleum (65% $SO_3$ content) are added dropwise over the course of 10 minutes, whilst cooling and stirring. Thereafter, the mixture is heated to 60° for 16 hours, cooled and poured out onto 750 parts of ice. After adding 1500 parts by volume of saturated sodium acetate solution and 600 parts by volume of saturated sodium chloride solution, the crystalline precipitate is filtered off, washed with dilute sodium chloride solution and dried at 60° in vacuo. 34 parts of the compound of the formula

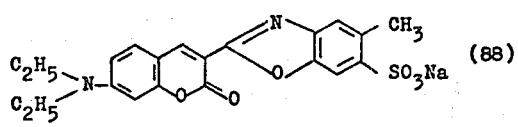
(88)

are obtained. Compound (88) shows a very intense green fluorescence in organic solvents such as dimethylformamide; in aqueous solution, on the other hand, the fluorescence is quenched.

Monosulphonated dyestuffs are also obtained if instead of the compound of the formula (2), equivalent quantities of one of the following coumarine dyestuffs are employed: compounds of the formula (3), (4), (5), (6), (10), (11), (12), (13), (14), (15), (16), (17), (18), (19), (20), (21), (22), (25), (26), (27), (28), (29), (31), (32), (33), (35), (36), (37), (39), (44), (45), (46), (47), (48), (49), (51), (52), (53), (54), (58), (59), (63), (64), (65), (68), (69), (70), (71), (72), (75) (76), (77), (78), (79) and (80).

Disulphonated dyestuffs, in addition to monosulphonated dyestuffs, are obtained if instead of the compound of the formula (2) equivalent quantities of one of the following coumarine dyestuffs are employed: compounds of the formula (7), (9), (23), (24), (40), (42), (43), (50), (61) and (74).

EXAMPLE 12b 25.7 parts of the compound of the formula

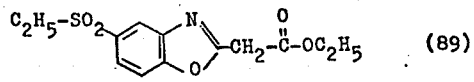
(89)

of melting point 110° – 111°, 19.5 parts of 4-diethylaminosalicylaldehyde, 300 parts by volume of ethanol and 2 parts by volume of piperidine are heated to the boil for 10 hours under reflux and whilst stirring, and are then cooled to room temperature. The crystalline precipitate is filtered off, washed with methanol and dried in vacuo at 70°. 36.5 parts of the compound of the formula (33) of melting point 186° – 188° (compare Example 2b !) are obtained.

If, instead of the compound (89), equivalent quantities of one of the following compounds are employed, the coumarine dyestuffs listed in the following Table are obtained:

Table:

| Oxazolyl-(2)-acetic ester | Coumarine Dyestuff |
|---|---|
| Benzoxazolyl-(2)-acetic acid ethyl ester | (4) |
| 5-Methyl-benzoxazolyl-(2)-acetic acid methyl ester | (2) |
| 5-Chloro-benzoxazolyl-(2)-acetic acid isopropyl ester | (31) |
| 5-Bromobenzoxazolyl-(2)-acetic acid methoxyethyl ester | (71) |
| Naphth[1,2-d]oxazolyl-(2)-acetic acid benzyl ester | (42) |

EXAMPLE 13b 13.9 parts of bis-(5-methyl-benzoxazolyl)-methane and 9.7 parts of 4-diethylamino-salicylaldehyde in 50 parts by volume of ethanol are briefly heated to 40° in the presence of 2 parts by volume of piperidine, whereby a clear reddish solution is produced from which a crystalline precipitate starts to separate out after about 1 hour. This precipitate is filtered off after 3 hours, washed with ice-cold methanol and drid at 60° in vacuo. 21.4 parts of compound of the formula

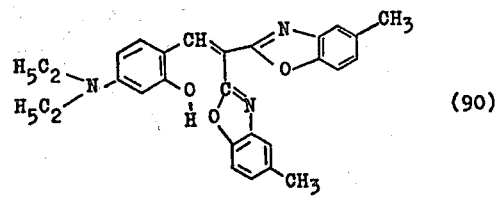
(90)

of melting point 223° – 224.5° are obtained.

Bis-(5-methyl-benzoxazolyl)-methane is manufactured in the following manner: 246 parts of 3-amino-4-hydroxytoluene 175 parts of malonic acid diethyl ester, 2 parts of boric acid and 400 parts of volume of o-dichlorobenzene are slowly heated under nitrogen, over the course of 4 hours, to an internal temperature of 220°, whilst allowing azeotropic mixtures of alcohol, water and dichlorobenzene, and finally pure dichlorobenzene, to distil off through a column. The resulting melt cake it recrystallised from 500 parts by volume of methanol. 153 parts of bis-(5-methyl-benzoxazolyl)-methane of melting point 91° are first obtained. A further 84 parts of the same degree of purity are obtained by concentrating the mother liquor.

The following bis-benzoxazolyl-methanes are manufactured analogously, using the appropriate starting components:

| | |
|---|---|
| Bis-benzoxazolyl-methane | melting point: 175–177° |
| Bis-(5-ethylsulphonyl-benzoxazolyl)-methane | melting point: 192–194° |
| Bis-(5,6-dimethyl-benzoxazolyl)-methane | melting point: 153–155° |
| Bis-(5-cyclohexyl-benzoxazolyl)-methane | melting point: 144–146° |
| Bis-(5-phenyl-benzoxazolyl)-methane | melting point: 135–136° |

EXAMPLE 14b 20 parts of the abovementioned compound (90) are introduced into 60 parts by volume of 96% strength sulphuric acid at 20° – 30°, with slight cooling, and the whole is stirred for 3 hours at 50°. The solution is then poured out onto 500 ml of water and 400 g of ice. The pH-value is adjusted to 5 by adding sodium hydroxide solution and ice, and the suspension is stirred for 5 hours. The crystalline precipitate is filtered off, washed with water and dried at 50° in vacuo, 15 parts of the compound of the formula

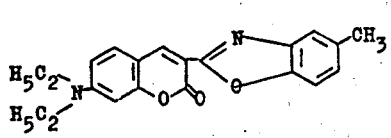

of melting point 204° – 206° (from dimethylformamide) are obtained.

EXAMPLE 15b 7.7 parts of 4-diethylamino-salicylaldehyde and 11.2 parts of bis(5-methylbenzoxazolyl)-methane are mixed and introduced in portions, over the course of 20 minutes, into 40 parts by volume of 96% strength sulphuric acid with slight cooling, and the whole is stirred for 4 hours at 50° – 60°. The solution is subsequently poured out onto a mixture of 200 parts by volume of water and 200 parts of ice. After standing for 12 hours, the precipitate is decanted, rinsed with water and recrystallised from 250 parts by volume of dimethylformamide. 7 parts of the benzoxazolyl-coumarine compound (2), described in the preceding example, of melting point 204° – 206° are obtained.

EXAMPLE 16b 9.7 parts of 4-diethylamino-salicyaldehyde and 13.9 parts of bis-(5methyl-benzoxazolyl)-methane in 50 parts by volume of ethanol, with the addition of 1 part by volume of pyrrolidine, are heated to the boil under reflux for 26 hours. After cooling, the crystalline precipitate is filtered off, washed with methanol and dried in vacuo at 60°. 14.6 parts of the compound of the formula (2) are obtained, melting at 204° – 206° after recrystallisation from dimethylformamide.

EXAMPLE 17b 9.7 parts of 4-diethylaminosalicylaldehyde and 21.7 parts of bis-(5-ethyl-sulphonylbenzoxazolyl)-methane (melting point 192° – 194°) in 50 parts by volume of n-butanol, with the addition of 1 part by volume of piperidine, are heated to the boil for 24 hours under reflux. 100 parts by volume of ethanol are then added at 100° C and the solution is allowed to cool slowly. The crystalline precipitate is filtered off, washed with methanol and dried at 60° in vacuo. 15.5 parts of the compound of the formula

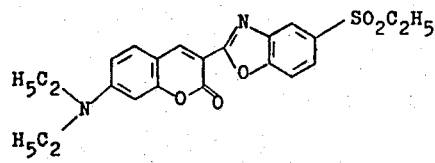

of boiling point 186° – 188° (from chlorobenzene) are obtained.

EXAMPLE 18b 49.2 parts of 3-amino-4-hydroxytoluene, 35 parts of malonic acid diethyl ester, 0.2 part of boric acid and 100 parts by volume of o-dichlorobenzene are slowly heated under nitrogen to an internal temperature of 230° over the course of 3 hours, whilst allowing azeotropic mixtures of alcohol, water and o-dichlorobenzene, and finally pure dichlorobenzene, to distill off through a column. The melt is left to cool to 150° and is treated with 100 parts by volume of n-butanol. 38 parts of 4-diethylamino-salicylaldehyde and 2 parts by volume of piperidine are added under nitrogen and the solution is heated to the boil for one-half hour under nitrogen and whilst stirring. 5 parts of p-toluenesulphonic acid are then added and the solution is heated to the boil for a further 3 hours. After cooling, the crystalline precipitate is filtered off, washed with methanol and dried in vacuo at 70°. 55.5 parts of the compound of the formula (2), melting point 204° – 206° (from dimethylformamide) are obtained.

EXAMPLE 19b

An approximately 0.25% strength dyeing with dyestuff (4) on polyethylene terephthalate fabric was produced as follows The fabric is introduced, at 50° and using a liquor ratio of 1:40, into a dyebath which contains the finely divided dyestuff, 2g/l of a conventional anionic dispersing agent, 5 g/l of o-cresotic acid methyl ester and 1 g/l of $NaH_2PO_4$ and which is adjusted to pH 4.5 – 5 with acetic acid. The temperature is raised to 80° – 85° over the course of 15 – 20 minutes and the system is left in this temperature range for a further 20 minutes. Thereafter, the liquor is gradually raised to the boil. After boiling for 1 – 1½ hours, the dyeing process is complete.

After rinsing and drying, greenish-tinged yellow dyeings of exceptional brilliance and very good fastness properties are obtained. (Greater brilliance, distinctly better affinity and better light fastness as compared to the nearest comparable dyestuff, 7-diethylamino-3-benzimidazolyl-(2)-coumarine (German Published Specification No. 1,098,125, Example 2)).

Greenish-tinged dyeings of outstanding brilliance are also obtained if instead of compound (4) one of the following dyestuffs is employed: the compound of the formula (2), (3), (5), (6), (7), (8), (10), (12), (13), (14), (15), (16), (17), (21), (29), (31), (32), (33), (34), (35), (40), (42), (43), (45), (46), (51), (52), (53), (54), (58), (59), (61), (63), (64), (65), (68), (69), (70), (71), (72), (75), (79), (85), and (86).

EXAMPLE 20b

An approximately 0.12% strength dyeing with dyestuff (2) on polyamide-6 fabrics was produced as follows The fabric is introduced, at 40° and using a liquor ratio of 1:40 to 1:30, into a dyebath which contains 1 g/l of a conventional anionic dispersing agent and the finely divided dyestuff. The liquor temperature is raised to 98° (boiling point) over the course of 40 – 60 minutes and left at this temperature for about a further 60 minutes. Thereafter, the fabric is rinsed and dried. Greenish-tinged yellow dyeings of high brilliance and very good fastness properties are obtained. Greenish-tinged dyeings of outstanding brilliance are also obtained if instead of the compound (2) one of the following dyestuffs is employed: the compound of the formula (3), (4), (5), (6), (7), (8), (9), (11), (12), (13), (14), (15), (17), (18), (19), (20), (21), (22), (25), (29), (31), (32), (35), (39), (40), (46), (47), (48), (49), (51), (52), (53), (54), (58), (59), (61), (63), (65), (68), (69), (70), (71), (72), (75), (78), (79), (85) and (86).

EXAMPLE 21b

Polyethylene terephthalate fabric is impregnated on a padder, at 40°, with an aqueous liquor which per liter contains 10 g of finely disperse coumarine dyestuff of the formula (2), 7.5 g of sodium alginate, 20 g of triethanol-amine and 20 g of octylphenyl-polyglycol-ether. The fabric is squeezed out to a liquor content of about 100%, dried at 100° and subsequently fixed for 30 seconds at 200°–210°. After rinsing and drying, an extremely brilliant, greenish-tinged dyeing of very good fastness properties is obtained.

EXAMPLE 22b

A fabric of polyethylene terephthalate is impregnated at room temperature with a clear padding liquor which contains 5.5 parts of dyestuff of the formula (58) in 994.5 parts of tetrachloroethylene. After squeezing out to a weight increase of 60%, the fabric is dried for one minute at 80°. Thereafter the dyestuff is fixed for 45 seconds at 220°. The fabric is rinsed in cold tetrachloroethylene for 20 seconds. After drying, an extremely brilliant greenish-tinged yellow dyeing having very good fastness properties is obtained. The fixing yield is 98%.

A dyeing of similar brilliance and again outstanding fastness properties is obtained if a clear padding liquor which contains 0.95 part of the compound (2) in 999 parts of perchloroethylene is used. The fixing yield is in this case 97% at 190° and 99% at 220°.

Further coumarine dyestuffs which are particularly suitable for dyeing from tetrachloroethylene correspond to the formula (6), (14), (20), (26), (27), (40), (51), (52), (53), (54), (59), (64), (70), (72) and (85).

EXAMPLE 23b 30 parts by weight of the disperse dyestuff of Example 19 b are dissolved in a mixture of 50 parts by weight of thiodiglycol, 20 parts by weight of printing oil and 160 parts by volume of water. The solution is diluted with 200 parts of water and thickened with 400 parts of crystal gum, and a printable paste is produced by means of a further 60 to 100 parts of water. Fabrics of polyethylene terephthalate are printed with this paste in the usual manner and are subsequently steamed for 20 minutes in a steamer at 103°–105°. After soaping, rinsing with water and drying, a very brilliant, greenish-tinged yellow coloured print is obtained, which is distinguished by good fastness to washing, rubbing, light and sublimation.

EXAMPLE 24 b 1 part of the dyestuff of the formula (2) is finely dispersed in 4000 parts of water with the aid of 8 parts of oleic acid N-methyltauride. 100 parts of cellulose triacetate fabric are subsequently introduced into the bath at 40°. The bath temperature is raised to 100° over the course of 30 minutes. Dyeing is carried out for 1.5 hours at the boil. After rinsing with warm water, followed by cold water, and drying, a very brilliant dyeing having very good fastness properties is obtained.

EXAMPLE 25b 0.16 part of the dyestuff of the formula (88) are dissolved in 160 parts of hot water, 50 parts by volume of 10% strength ammonium acetate solution are added and the whole is diluted with water to a liquor weight of 5000 parts. Thereafter, 100 parts of poly-ε-caprolactam fabric are introduced into the dyebath at 50°, and the bath is heated to 100° over the course of 15 minutes. The dyebath is kept at this temperature for 1 hour, but after 30 minutes 3 g of acetic acid are further added. After rinsing and drying, a very brilliant greenish-tinged yellow dyeing having very good fastness properties is obtained.

Dyeings of similarly high brilliance and fastness are obtained if instead of the dyestuff of the formula (88) one of the other monosulphonated or disulphonated dyestuffs described in Example 11 b is employed.

EXAMPLE 26b 0.2 part of the dyestuff of the formula (88) are dissolved in 200 parts of hot water and diluted with water to a liquor weight of 5000 parts. Thereafter 100 parts of wool fibres are introduced into the dyebath at 40°, 3 parts of acetic acid are added, the bath is heated to the boil over the course of 15 minutes and dyeing is carried out for 1 hour at the boil, further adding 2 parts of formic acid after 30 minutes. After rinsing and drying, a brilliant greenish-tinged yellow dyeing having good fastness properties is obtained.

Dyeings of similarly high brilliance and fastness are obtained if instead of the dyestuff of the formula (88) one of the other monosulphonated or disulphonated dyestuffs described in Example 11 b is employed.

I claim:
1. Oxazolyl-courmarine having the formula

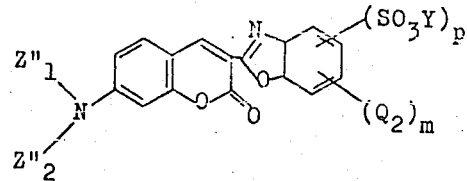

wherein $Q_2$ is $C_1$–$C_5$-alkyl; ;chlorine; $C_1$–$C_5$-alkoxy; cyclohexyl; phenyl; benzyl; phenethyl; phenoxy; $C_1$–$C_5$-alkylcarbonylamino; phenylcarbonylamino; $C_1$–$C_5$-alkylsulfonylamino; phenylsulfonylamino; $C_1$–$C_5$-alkylsulfonyl; phenylsulfonyl; —$SO_2V_2$ or —$CONV_2$; wherein V is hydrogen or $C_1$–$C_2$-alkyl;
$Z''_1$ and $Z''_2$ independently of one another are $C_1$–$C_5$-alkyl; $C_1$–$C_5$-alkyl substituted by mono-chlorine, mono-bromine, mono-nitrile, mono-hydroxyl or mono-$C_1$–$C_4$-alkoxy; or $Z''_1$ and $Z''_2$ are the remaining members of a pyrrolidine, piperidine or morpholine radical;
Y is hydrogen, sodium, potassium, lithium, ammonium or the cation of a basic dyestuff;
p is 0 or 1; and
m is 0, 1 or 2.
2. Ozazolyl-coumarine having the formula

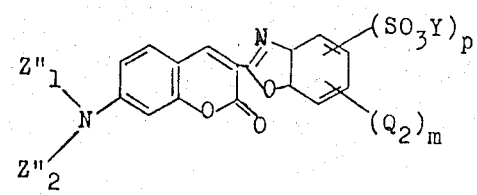

wherein $Q_2$ is $C_1$–$C_5$-alkyl; chlorine; $C_1$–$C_5$-alkoxy; cyclohhexyl; phenyl; benzyl; phenethyl; phenoxy; $C_1$–$C_5$-alkylcarbonylamino; phenylcarbonylamino; $C_1$–$C_5$-alkylsulfonylamino; phenylsulfonylamino; $C_1$–$C_5$-alkylsulfonyl; phenylsulfonyl; —$SO_2V_2$ or —$CONV_2$; wherein V is hydrogen or $C_1$–$C_2$-alkyl;

$Z''_1$ and $Z''_2$ independently of one another are $C_1$–$C_5$-alkyl; $C_1$–$C_5$-alkyl substituted by mono-chlorine, mono-bromine, mono-nitrile, mono-hydroxyl or mono-$C_1$–$C_4$-alkoxy; or $Z''_1$ and $Z''_2$ are the remaining members of a pyrrolidine, piperidine or morpholine radical;

Y is hydrogen, sodium, potassium, lithium or ammonium;

p is 0 or 1; and m is 0, 1 or 2.

3. Oxazolyl-coumarine having, in the free acid form, the formula

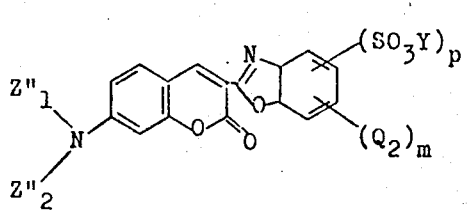

wherein $Q_2$ is $C_1$–$C_5$-alkyl; chlorine, $C_1$–$C_5$-alkoxy; cyclohexyl; phenyl; benzyl; phenethyl; phenoxy; $C_1$–$C_5$-alkylcarbonylamino; phenylcarbonylamino; $C_1$–$C_5$-alkylsulfonylamino; phenylsulfonylamino; $C_1$–$C_5$-alkylsulfonyl; phenylsulfonyl; —$SO_2V_2$ or —$CONV_2$; wherein V is hydrogen or $C_1$–$C_2$-alkyl;

$Z''_1$ and $Z''_2$ independently of one another are $C_1$–$C_5$-alkyl; $C_1$–$C_5$-alkyl substituted by mono-chlorine, mono-bromine, mono-nitrile, mono-hydroxyl or mono-$C_1$–$C_4$-alkoxy; or $Z''_1$ and $Z''_2$ are the remaining members of a pyrrolidine, piperidine or morpholine radical;

Y is hydrogen;

p is 0 or 1; and m is 0, 1 or 2.

4. Oxazolyl-coumarine of claim 1 wherein $Q_2$ is $C_1$–$C_5$-alkyl; chlorine; $C_1$–$C_5$-alkoxy; cyclohexyl; phenyl; benzyl; phenethyl; or phenoxy;

$Z''_1$ and $Z''_2$ independently of one another are $C_1$–$C_5$ alkyl;

p is 0 or 1; and m is 0, 1 or 2.

5. Oxazolyl-coumarine of claim 1 wherein $Q_2$ is $C_1$–$C_5$-alkyl; chlorine; $C_1$–$C_5$-alkoxy; cyclohexyl; phenyl; benzyl; phenethyl; or phenoxy; $Z''_1$ and $Z''_2$ independently of one another are $C_1$–$C_5$-alkyl;

p is 0; and m is 1.

6. Oxazolyl-coumarine of claim 2 having the formula

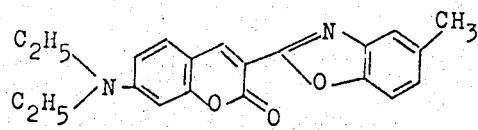

7. Oxazolyl-coumarine of claim 1 having the formula

8. Oxazolyl-coumarine of claim 1 having the formula

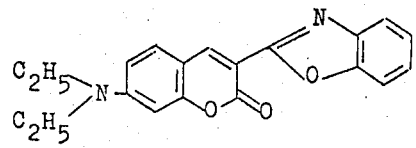

9. Oxazolyl-coumarine of claim 1 having the formula

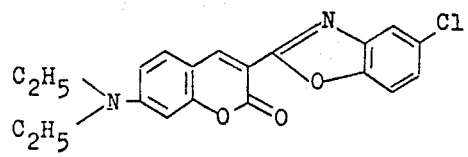

10. Oxazolyl-coumarine of claim 1 having the formula

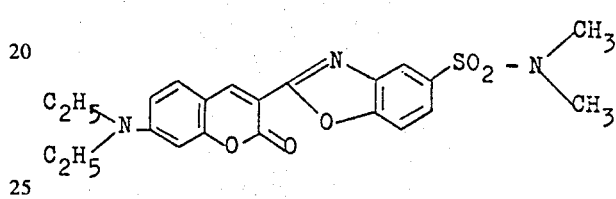

11. Oxazolyl-coumarine of claim 1 having the formula

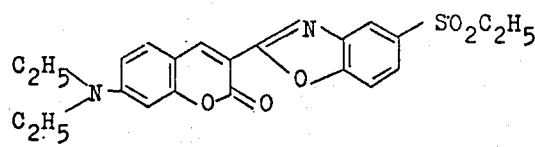

12. Oxazolyl-coumarine of claim 1 having the formula

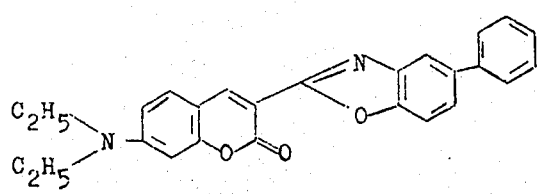

13. Oxazolyl-coumarine of claim 1 having the formula

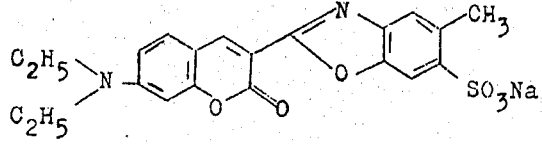

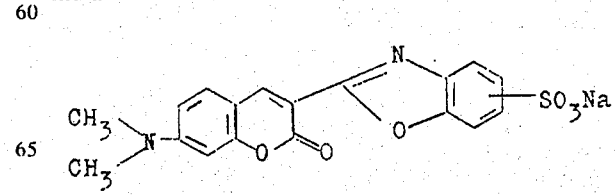

* * * * *